United States Patent
Chou et al.

(10) Patent No.: US 8,062,488 B2
(45) Date of Patent: Nov. 22, 2011

(54) BIOSENSOR CONTAINING RUTHENIUM, MEASUREMENT USING THE SAME AND THE APPLICATION THEREOF

(75) Inventors: Jung-Chuan Chou, Douliou (TW); Shih-I Liu, Kaohsiung (TW)

(73) Assignee: National Yunlin University of Science and Technology, Yunlin (TW)

( * ) Notice: Subject to any disclaimer, the term of this patent is extended or adjusted under 35 U.S.C. 154(b) by 369 days.

(21) Appl. No.: 12/508,458

(22) Filed: Jul. 23, 2009

(65) Prior Publication Data

US 2009/0283805 A1 Nov. 19, 2009

Related U.S. Application Data

(62) Division of application No. 11/449,936, filed on Jun. 9, 2006, now Pat. No. 7,754,056.

(30) Foreign Application Priority Data

Nov. 1, 2005 (TW) ................................ 94138247 A

(51) Int. Cl.
*G01N 27/414* (2006.01)
*C12M 1/40* (2006.01)

(52) U.S. Cl. ......... 204/403.01; 204/403.03; 204/403.14; 204/416; 204/403.04; 435/287.1; 435/287.3; 435/817; 257/253; 257/288

(58) Field of Classification Search ............ 204/403.01, 204/403.03, 403.04, 403.14, 416; 435/287.1, 435/287.3, 817; 257/253, 288
See application file for complete search history.

(56) References Cited

U.S. PATENT DOCUMENTS

| | | | | |
|---|---|---|---|---|
| 6,280,587 B1 * | 8/2001 | Matsumoto | ............. | 204/403.01 |
| 7,431,811 B2 * | 10/2008 | Chou et al. | .................... | 204/291 |
| 7,582,500 B2 * | 9/2009 | Chou et al. | ....................... | 438/49 |
| 7,598,546 B1 * | 10/2009 | Chou et al. | .................... | 257/253 |
| 7,754,056 B2 * | 7/2010 | Chou et al. | ............... | 204/192.15 |

* cited by examiner

*Primary Examiner* — Bruce Bell

(57) ABSTRACT

A biosensor containing ruthenium, measurement using the same, and the application thereof. The biosensor comprises an extended gate field effect transistor (EGFET) structure, including a metal oxide semiconductor field effect transistor (MOSFET), a sensing unit comprising a substrate, a layer comprising ruthenium on the substrate, and a metal wire connecting the MOSFET and the sensing unit.

10 Claims, 31 Drawing Sheets

BIOSENSOR CONTAINING RUTHENIUM, MEASUREMENT USING THE SAME AND THE APPLICATION THEREOF

This application is a divisional of U.S. application Ser. No. 11/449,936, filed Jun. 9, 2006, now U.S. Pat. No. 7,754,056 the entire disclosure of which is hereby incorporated by reference.

BACKGROUND OF THE INVENTION

1. Field of the Invention

The invention relates to a biosensor, and in particular to a biosensor comprising a ruthenium nitride or ruthenium oxide film and the application thereof.

2. Description of the Related Art

The Ion Sensitive Field Effect Transistor (ISFET), first proposed by Piet Bergveld in 1970, is similar to the conventional MOSFET (Metal-Oxide-Semiconductor Field Effect Transistor) except that a sensitive film is used in place of the metal gate of the MOSFET. The extended gate ion sensitive field effect transistor (EGISFET) developed from ISFET combines the extended gate containing a sensing membrane with the MOSFET by a conducting wire and has the advantages of simple structure, easy package procedure, low cost, and flexibility in biomedical application. In addition, EGISFET can be prepared with the CMOS standard process and the obtained EGISFET has higher sensitivity in detecting pH value of a solution. However, the sensing membranes presently in use, including $IrO_2$ and $SnO_2$, are not materials for the CMOS standard process.

Patents related to the manufacture of ISFET include U.S. Pat. Nos. 6,409,909 and 6,326,215. U.S. Pat. No. 6,409,909 discloses a modular, in particular multidimensional system for the reagent-free continuous detection of a substance. This system is characterized by the presence of at least two measuring modules of preferably different types. The modules are robust and designed for a long-time operation. An exchangeable or replaceable selective layer structure is included. The system may also include appropriate modules for amperometry and optical sensors. U.S. Pat. No. 6,326,215 discloses a sensor for sensing the presence of an analyte without relying on redox mediators. This sensor includes (a) a plurality of conductive polymer strands each having at least a first end and a second end each aligned in a substantially common orientation; (b) a plurality of molecular recognition headgroups having an affinity for the analyte and being attached to the first ends of the conductive polymer strands; and (c) an electrode substrate attached to the conductive polymer strands at the second ends. The electrode substrate is capable of reporting to an electronic circuit reception of mobile charge carriers (electrons or holes) from the conductive polymer strands. The electrode substrate may be a photovoltaic diode. Also disclosed is a method of forming a sensor capable of sensing the presence of an analyte component. This method includes (a) contacting a sensor substrate (e.g., a device element of a device on semiconductor chip) with a first medium containing mobile conductive polymer strands or precursors of the conductive polymer strands; (b) applying a first potential to the substrate sufficient to form a first structure having the conductive polymer strands affixed into the substrate; (c) contacting the sensor substrate, with affixed conductive polymer strands, with a second medium containing mobile molecular recognition headgroups; and (d) applying a second potential to the substrate sufficient to affix the molecular recognition headgroups to the affixed conductive polymer strands.

U.S. Pat. No. 6,218,208 to the inventors discloses a sensitive material-tin oxide ($SnO_2$) obtained by thermal evaporation or by RF reactive sputtering used as a high-pH-sensitive material for a Multi-Structure Ion Sensitive Field Effect Transistor (ISFET). The multi-structure ISFET has high performances such as a linear pH sensitivity of approximately 56-58 mV/pH in a concentration between pH 2 and pH 10. A low drift characteristic of approximately 5 mV/day, response time of less than 0.1 second, and an isothermal point of this ISFET sensor can be obtained if the device operates with an adequate drain-source current. In addition, this ISFET sensor has other advantages, such as inexpensive fabrication, low cost, and mass production characteristics.

In addition, U.S. Pat. No. 5,911,873 discloses an apparatus for measuring ion concentration of a solution, comprising an ion sensitive field effect transistor (ISFET), a reference device, an ISFET control circuit, a memory, a measurement circuit and a diagnostic circuit. The ISFET has a drain, a source, an ion sensitive gate region and a plurality of device characteristics. The reference device is separated from the gate region by a sample solution. The ISFET control circuit is coupled to the ISFET and operates the ISFET at a drain-source voltage $V_{DS}$ and at n successive drain currents $I_{Di}$ and corresponding gate-source voltages $V_{GSi}$, wherein I is an integer from 1 to n and n is an integer greater than 1. The memory stores the plurality of device characteristics and the n successive drain currents $I_{Di}$ and gate-source voltages $V_{GSi}$. The measurement circuit measures ion concentration of the solution as a function of at least one of the n successive drain currents $I_{Di}$ and gate-source voltages $V_{GSi}$ and the plurality of device characteristics stored in the memory. The diagnostic circuit measures at least one of the device characteristics of the ISFET as a function of the n successive drain currents $I_{Di}$ and gate-source voltages $V_{GSi}$. U.S. Pat. No. 5,384,028 discloses a biosensor, provided with a memory for storing data including data and time of fabrication of the biosensor, lot number of the biosensor, effective period of the biosensor, biosensor characteristics, and administrative data of the biosensor. The memory may store additional data such as the measured data, the consecutive (total) measuring time, the measured results, etc. U.S. Pat. No. 5,309,085 discloses a measuring circuit with a biosensor utilizing ion sensitive field effect transistors having a simplified structure, advantageous to integration. The measuring circuit comprises two ion sensitive FET input devices composed of an enzyme FET having an enzyme sensitive membrane on the gate and a reference FET, and a differential amplifier for amplifying the outputs of the enzyme FET and the reference FET. The drift phenomena of the ISFETs from use of a non-stable quasi-reference electrode as well as the temperature dependence thereof can be eliminated by the differential amplifier consisting of MOSFETs having the same channel as the ISFETs. The ISFET biosensor and the measuring circuit can be integrated into one chip.

Conventional electrochemical systems having three electrodes employ (1) a working electrode, (2) a reference electrode, and (3) a counter electrode. The reaction at the working electrode is monitored and controlled. The functions of the reference and counter electrodes ensure that the working electrode actually experiences the desired conditions, i.e. the correct potential to be applied. The reference electrode measures the potential at the interface of the working electrode and the sample as accurately as possible. In an ideal situation, no current passes through the reference electrode. The counter electrode ensures that the correct potential difference between the reference electrode and the working electrode is being applied. The potential difference between the working electrode and the reference electrode is assumed to be the same as the desired potential at the working electrode. If the potential measured at the working electrode is not the potential desired at the working electrode, the potential applied between the counter electrode and working electrode is altered accordingly, i.e., the potential is either increased or decreased. The reaction at the counter electrode is also equal and opposite to the charge transfer reaction occurring at the working electrode, i.e., if an oxidation reaction is occurring at the working electrode then a reduction reaction will take place at the counter electrode, thereby allowing the sample to remain electrically neutral.

In the ISFET applications, however, many factors such as hysteresis, temperature, and drift behavior affect the accuracy of the measuring results. The variation of the temperature leads to a deviation in measurement due to ion sorption of a sensing membrane differing at various temperatures. With reference to the hysteresis behavior, it is related to the change in the pH of the solution (such as pHx→pHy→pHx→pHz→pHx) and the corresponding change in the output voltage of the ISFET (such as Vox1→Voy→Vox2→Voz→Vox3). At the same pH, the difference between the first output voltage and the final output voltage (such as Vox3→Vox1) is defined as the hysteresis width. For drift behavior, the drift rate is defined as the change in the gate voltage per unit time under conditions in which the source-drain current is stable and the temperature is constant after the intrinsic response of the pH-ISFET is completed. Hence, there is a need to measure the three effects to prevent error.

Various materials are used as the sensing membrane of ISFET and EGISFET, such as $Al_2O_3$, $Ta_2O_5$, $Si_3N_4$, $SnO_2$, and the like. These materials can be prepared by sputtering or plasma chemical vapor deposition, however, they still have some drawbacks in practice. A sensing film with low cost and simple process is, however, still required for commercial application.

BRIEF SUMMARY OF THE INVENTION

A detailed description is given in the following embodiments with reference to the accompanying drawings.

The invention provides a biosensor comprising an extended gate field effect transistor (EGFET) structure with a ruthenium oxide ($RuO_x$) or ruthenium nitride (RuN) sensing membrane prepared by radio frequency (RF) sputtering.

The invention further provides a low cost process for the preparation of $RuO_x$ or RuN film for ISFET by RF sputtering deposition.

The invention also provides a system of measuring pH value in a solution including the biosensor. A curve for the gate voltage versus source/drain current of the biosensor in the solution can be measured and the sensitivity of the biosensor obtained.

Accordingly, an embodiment of the biosensor comprises an extended gate ion sensitive field effect transistor (EGISFET). The biosensor includes a metal oxide semiconductor field effect transistor (MOSFET), an extended gate as a sensing unit including a substrate and a ruthenium-containing film thereon, and a conductive wire connecting the MOSFET and the sensing unit. In one embodiment of the biosensor, the ruthenium-containing film is a $RuO_x$ or RuN film.

An embodiment of a preparation of a biosensor, comprising an extended gate ion sensitive field effect transistor (EGISFET), includes providing an extended gate ion sensitive field effect transistor comprising an extended gate region and forming a ruthenium-containing film on the extended gate region by radio frequency (RF) sputtering deposition to obtain a biosensor.

A system for measuring pH in a solution includes the disclosed biosensor, a reference electrode supplying stable voltage, a semiconductor characteristic instrument connecting the biosensor and the reference electrode respectively, a temperature controller including a temperature control center, a thermocouple, and a heater, and a light-isolation container isolating the sensing unit from photosensitive effect. The temperature control center connects the thermocouple and the heater, respectively. pH measurement of a solution includes pouring a solution into the light-isolation container, immersing the sensing unit of the biosensor, the reference electrode, and the thermocouple in the solution, temperature adjustment of the solution by the heater controlled by the temperature control center after detection of temperature variation in the solution by the thermocouple, transmitting measurement data from the biosensor and the reference electrode to the semiconductor characteristic instrument, and reading out current-voltage (I-V) values of the solution by the semiconductor characteristic instrument to obtain pH value of the solution.

A method of measuring sensitivity of the biosensor using the disclosed system includes immersing the sensing unit of the biosensor in an acidic or basic solution, recording a curve of source/drain current versus gate voltage of the biosensor by the semiconductor characteristic instrument after altering pH values of the acidic or basic solution at a fixed temperature, and examining the curve to obtain a sensitivity of the biosensor at the fixed temperature and a fixed current.

A vitamin C biosensor is also provided, comprising an extended gate ion sensitive field effect transistor (EGISFET), including a metal oxide semiconductor field effect transistor (MOSFET), a first extended gate as a first sensing unit including a first substrate and a first ruthenium-containing film thereon, a second extended gate as a second sensing unit including a second substrate, a second ruthenium-containing film thereon, and a ascorbate oxidase film immobilized on the second ruthenium-containing film, and a conductive wire connecting the MOSFET, the first and the second sensing units. The vitamin C biosensor utilizes the first sensing unit for pH detection and the second sensing unit for detection of vitamin C concentration.

The RF sputtering deposition can be performed with a ruthenium target supplied with $O_2$ or $N_2$. In a preferred preparation of ruthenium oxide film at room temperature (25° C.), the ruthenium oxide film may have a linear sensitivity of 56.52 mV/pH in an average range of pH 1 to pH 12. In a preferred preparation of ruthenium nitride film at room temperature (25° C.), the ruthenium nitride film may have a linear sensitivity of 58.52 mV/pH in an average range of pH 1 to pH 13. The embodiment of the ruthenium-containing film prepared under a preferred condition can be analyzed by scanning electron microscope (SEM), atomic force microscope (AFM), electron spectroscope for chemical analysis (ESCA), energy dispersive spectrometer (EDS), or X-ray diffraction (XRD). The measurement of pH in a solution can be obtained by reading the current-voltage (I-V) values using the semiconductor characteristic instrument Keithley 236 and the amplifier LT1167. The temperature, enzyme, drift, and hysteresis behaviors of the embodiment of the ruthenium-containing film can be analyzed. The ruthenium-containing film may be further combined with IC process or micro-electromechanical systems (MEMS) for biochemical measurement.

BRIEF DESCRIPTION OF THE DRAWINGS

The invention can be more fully understood by reading the subsequent detailed description and examples with references made to the accompanying drawings, wherein:

FIG. 54A is a cross-section, and FIG. 54B is a front view.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Preparation of a biosensor, the prepared biosensor, a system comprising the same, and measurement using the system are provided.

Figure 1:
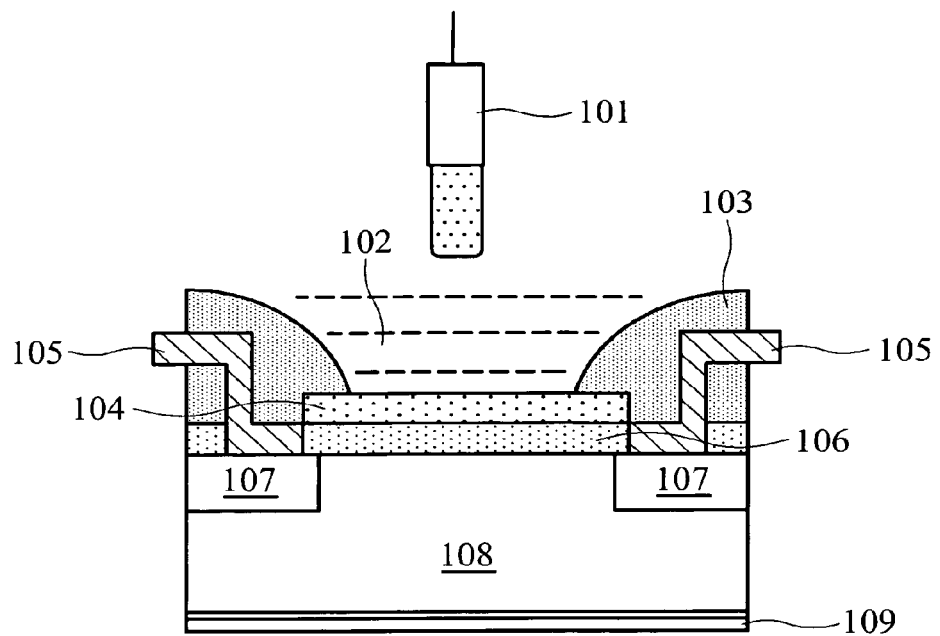
FIG. 1 is a cross section of an embodiment of a biosensor.

Ion Sensitive Field Effect Transistor (ISFET) is prepared by removing metal from the gate of Metal-Oxide-Semiconductor Field Effect Transistor (MOSFET) and forming a sensing film on the gate oxide to act as a sensing unit. Referring to FIG. 1, a conventional ion sensitive field effect transistor (ISFET) comprises a p-type silicon substrate 108, a gate comprising a silicon dioxide film 106 on the substrate 108, and a sensing film 104 immobilized on the silicon dioxide film 106, wherein only the sensing film 104 directly contacts a test solution 102. Other elements of the ISFET are covered by an insulation region 103 comprising epoxy resin. The sensing film 104 can be $Al_2O_3$, $Si_3N_4$, $Ta_2O_5$, $WO_3$, a-Si:H, $SnO_2$, or a-C:H. The sensitivity ranges from 50 to 58 mV/pH. Both sides of the silicon dioxide film 106 in the substrate are n-type heavy doped regions (source/drain) 107. A conductive wire 109, such as aluminum wire, connects the transistor such that source/drain electronic signals can be transmitted to additional circuits thereby after the test solution 102 is detected by the sensing film 104. In addition, a reference electrode 101 supplying stable voltage avoids noise disturbance. Detection by an ISFET comprises sensing film being exposed to an acidic or basic solution, and adsorbent hydrogen ions of the sensing film converted to electronic signals. Threshold voltage of the ISFET is then controlled by the electronic signals. Finally, hydrogen ion concentration is obtained by examining current values.

Extended Gate Field Effect Transistor (EGFET) was first proposed by J. Van Der Spiegel et al. ("The Extended Gate Chemical Sensitive Field Effect Transistor ad Multi-Species Microprobe." Sensors and Actuators B, 4:291-298, 1983). The structure consists of an integrated coaxial cable whose signal line is connected to a high input impedance electrometer with the shield boot-strapped to reduce capacitive charging effects. The electrometer is an on-chip source follower, designed for minimum input capacitance. The coaxial line, an extension of the gate of the transistor, is fabricated with a triple poly-silicon NMOS process. The entire structure is compatible with current IC technology and allows integration of on-chip signal conditioning circuitry. Units of four element probes, each covered with a different membrane such as $IrO_x$, AgCl, or $Ag_2S$, have been fabricated for the detection of $H^+$, $F^-$, $Cl^-$, and $Ag^+$ ions. The inventors, working with the EGFET structure, and discovered new sensing films of ruthenium oxide or ruthenium nitride.

Figure 3:
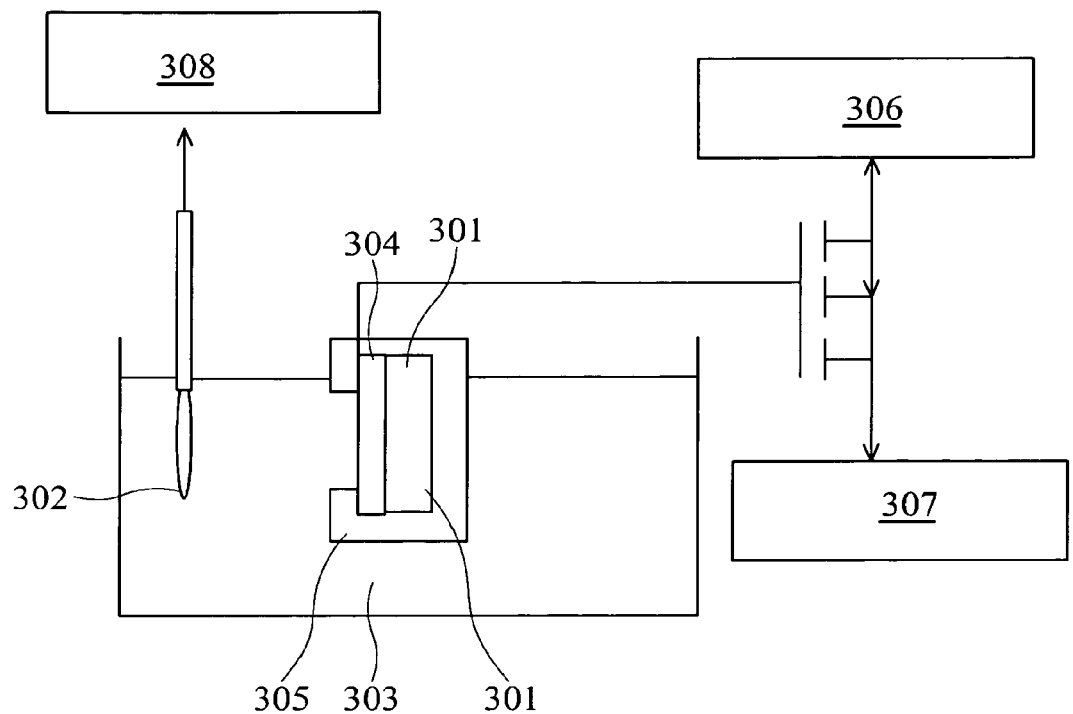
FIG. 3 shows a cross section of an extended gate structure of an embodiment of a biosensor.

An extended gate field effect transistor (EGFET) is developed from an ISFET. A sensing film is isolated from a gate of an ISFET, that is, a metal oxide semiconductor field effect transistor (MOSFET) is completely isolated from a test solution to prevent unstable characteristics on semiconductor elements and decrease interference from the test solution. Referring to FIG. 3, an extended gate field effect transistor comprises a sensing unit and an n-type MOSFET, wherein the sensing unit comprises a p-type (100) silicon substrate 301, and a ruthenium-containing sensing film 304 on the p-type silicon substrate 301. A conductive wire connects the sensing unit and the gate of the MOSFET which connects to a semiconductor characteristic instrument (306, 307). The sensing unit is covered by an insulation region 305, exposing partial sensing film 304 to contact a test solution. A reference electrode 302 connected to a semiconductor characteristic instrument 308 is still required for stable voltage avoiding noise disturbance. This structure is not sensitive to light and can be easily packaged and prepared. In addition, the structure can be designed as a disposable sensor. Noise disturbance can be greatly reduced when this device combines with an amplifier for real-time detection of pH. For an EGFET, a sensing film with high resistance may be regarded as a capacitor and parasitic capacitance is of concern. Candidates of the sensing film therefore should have low resistance and high capacitance to reduce noise disturbance.

Ruthenium is a noble metal with oxide forms having energy storage properties of high capacitance due to energy storage by the electric double layer and pseudo-capacitance by the redox reaction. The energy density of pseudo-capacitance is five to ten times that of double layer capacitance. Accordingly, ruthenium dioxide has low resistance (less than $10^{-4}$ ohm-cm) and high surface area (about 800-1000 $m^2$/g in hydrate). Ruthenium oxide is used because it has many advantages, such as (1) high conductance, (2) high superficial area, (3) multi-redox-active pairs [Ru(II)-Ru(III)-Ru(IV)-RU(V)-Ru(VI)-Ru(VII)], (4) excellent adhesion of enzymes and compounds, (5) excellent reversibility in electrochemistry, (6) high stability in acidic solution, and (7) good pH sensitivity. In the embodiment of the biosensor of the invention, ruthenium oxide is deposited by sputtering, which can be performed at low temperature for semiconductor manufacture and is beneficial for integration, has a high yield rate and composition that is easily controlled, and provides a sensing membrane with even distribution.

ISFET still has drawbacks such as temperature, drift, and hysteresis. The lifespan of ISFET is limited and the preparation costly. A disposable biosensor with low cost is provided to reduce noise and contamination. In addition, the biosensor of the invention utilizes a EGFET structure, superior to ISFET in that the structure can be miniaturized for trace detection, the structure is similar to MOSFET with the advantages of high input resistance and low output resistance, the structure has a quick response time, can be simply packaged, is not sensitive to light, and can be easily prepared at low cost.

Accordingly, an embodiment of a biosensor comprises an extended gate ion sensitive field effect transistor (EGISFET), including a metal oxide semiconductor field effect transistor (MOSFET), an extended gate to act as a sensing unit including a substrate and a ruthenium-containing film thereon, and a conductive wire connecting the MOSFET and the sensing unit. In an embodiment of a biosensor, the ruthenium-containing film is a $RuO_x$ or RuN film.

An embodiment of a preparation method for a biosensor comprising an extended gate ion sensitive field effect transistor (EGISFET) includes providing an extended gate ion sensitive field effect transistor comprising an extended gate region and forming a ruthenium-containing film on the extended gate region by radio frequency (RF) sputtering deposition to obtain a biosensor.

In an embodiment, the metal-oxide semiconductor field effect transistor (MOSFET) is an N-type FET. The conductive wire connects the gate of the MOSFET and the sensing film. The substrate is silicon substrate. In addition, the biosensor further includes an insulating layer covered the sensing unit, wherein the insulating layer is epoxy resin. Epoxy resin has good insulation, low permeability to water and electrolytes, excellent machinability, and excellent adhesion to sensing membrane, silicon chip, and substrate. In addition, epoxy resin is chemically stable and resistant to erosion. It also has low volume changes under different conditions.

The RF sputtering is performed at a pressure of 5~30 mtorr and power of 80~120 W, preferably 5~10 mtorr and 90~110 W, more preferably 10 mtorr and 100 W. For preparation of the ruthenium oxide film, the ratio of argon and oxygen ranges is 30~40:10~20 sccm, preferably 40:15 sccm. For preparation of the ruthenium nitride film, the ratio of argon and nitrogen ranges is 10~20:20~40 sccm, preferably 15:30 sccm. The working pressure ranges is $10^{-6}10\times10^{-6}$ torr, preferably $5\times10^{-6}$ torr.

A system of measuring pH in a solution includes the disclosed biosensor, a reference electrode supplying stable voltage, a semiconductor characteristic instrument connecting the biosensor and the reference electrode respectively, a temperature controller including a temperature control center, a thermocouple, and a heater, and a light-isolation container isolating the sensing unit from photosensitive effect. The temperature control center connects the thermocouple and the heater, respectively. Measurement of pH of a solution includes pouring a solution into the light-isolation container, immersing the sensing unit of the biosensor, the reference electrode, and the thermocouple in the solution, adjusting temperature of the solution by the heater controlled by the temperature control center after detecting temperature variation in the solution by the thermocouple, transmitting measurement data from the biosensor and the reference electrode to the semiconductor characteristic instrument, and reading out current-voltage (I-V) values of the solution by the semiconductor characteristic instrument to obtain pH value of the solution.

In an embodiment of the measuring system, the semiconductor characteristic instrument is Keithyley 236. The temperature is controlled at 25° C. The reference electrode is Ag/AgCl electrode. In addition, the light-isolation container is a dark box.

A method of measuring sensitivity of the biosensor using the disclosed system is also provided. The method includes immersing the sensing unit of the biosensor in an acidic or basic solution, recording a curve of source/drain current versus gate voltage of the biosensor by the semiconductor characteristic instrument after altering pH values of the acidic or basic solution at a fixed temperature, and examining the curve to obtain a sensitivity of the biosensor at the fixed temperature and a fixed current.

In an embodiment of the measuring method, the pH range from pH 1 to pH 12 for ruthenium oxide film and from pH 1 to pH 13 for ruthenium nitride film. In addition, the semiconductor characteristic instrument supplies a fixed voltage of 0.2V to a source/drain of the metal oxide semiconductor field effect transistor of the extended gate field effect transistor.

A vitamin C biosensor is also provided, comprising an extended gate ion sensitive field effect transistor (EGISFET), including a metal oxide semiconductor field effect transistor (MOSFET), a first extended gate to act as a first sensing unit including a first substrate and a first ruthenium-containing film thereon, a second extended gate to act as a second sensing unit including a second substrate, a second ruthenium-containing film thereon, and an ascorbate oxidase film immobilized on the second ruthenium-containing film, and a conductive wire connecting the MOSFET, the first and the second sensing unit. The vitamin C biosensor utilizes the first sensing unit for pH value detection and the second sensing unit for the detection of vitamin C concentration.

In an embodiment of the vitamin C biosensor, the MOSFET is N-type FET. The conductive wire connects the gate of the MOSFET and the first and the second sensing films. The first and second substrates are silicon substrate. The first and the second ruthenium-containing films can be $RuO_x$ or RuN films. The ascorbate oxidase is immobilized on the ruthenium-containing film by 3-glycidoxypropyltrimethoxysilane (GPTS) and the GPTS is premixed with toluene in a ratio of 10:90 by volume. The first sensing film is for detection of pH and the second sensing film is for detection of the concentration of vitamin C. In addition, the biosensor further includes an insulating layer covered the sensing unit, wherein the insulating layer is epoxy resin.

Figure 54A:
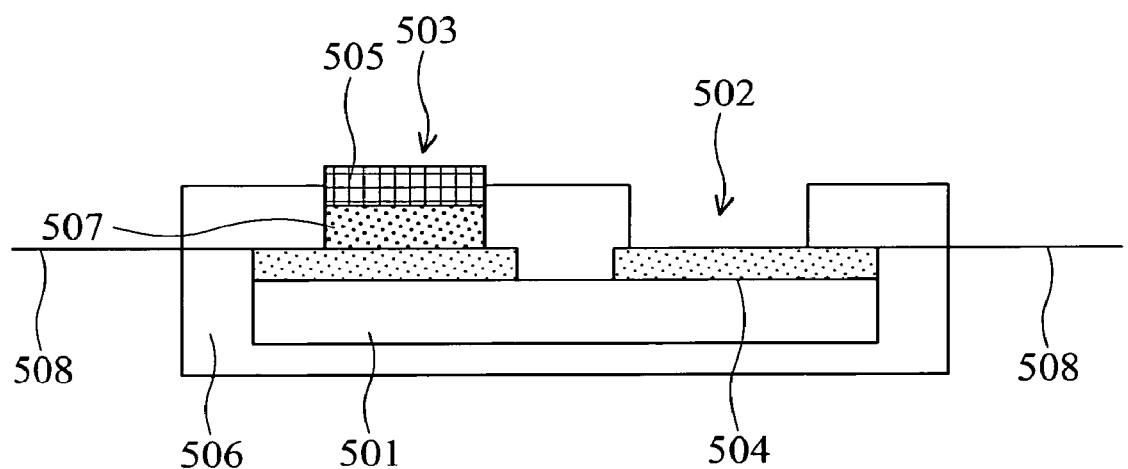
FIGS. 54A and 54B show a structure of an embodiment of a ruthenium-containing device combined with ascorbate oxidase.
Figure 54B:
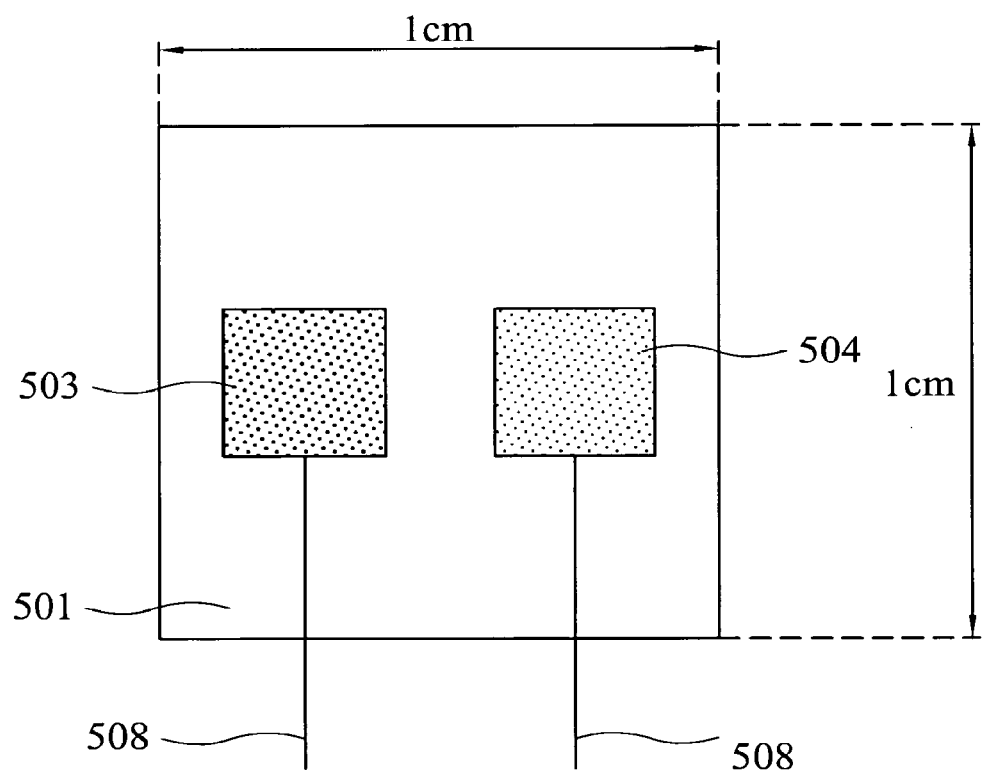
Figure 55:
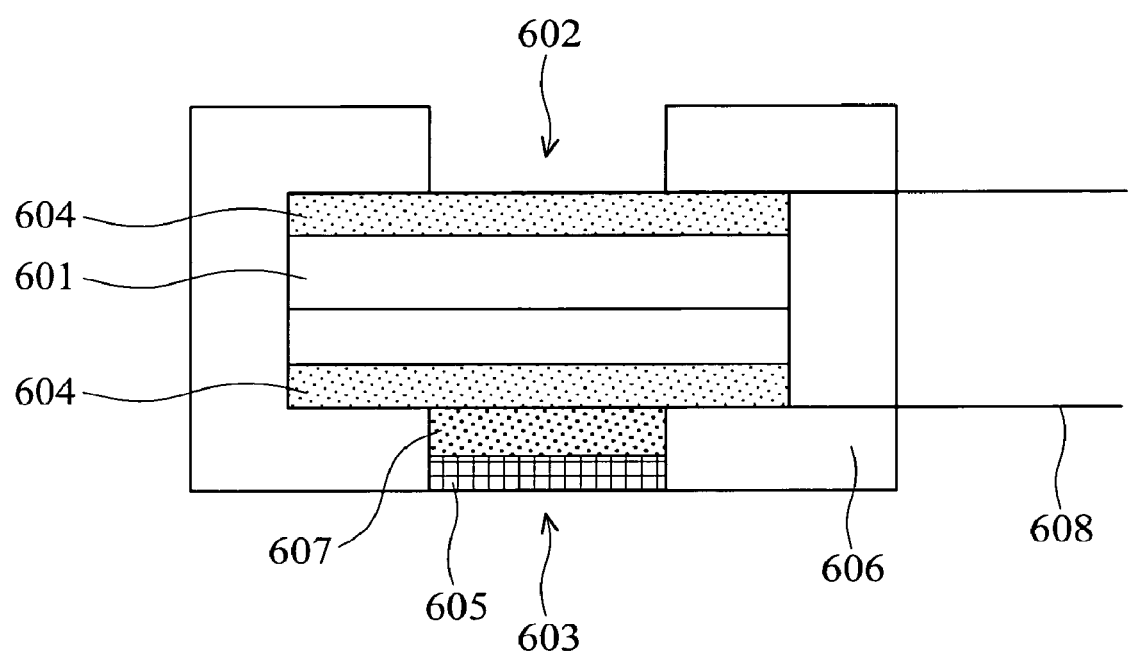
FIG. 55 is a cross section of another embodiment of the ruthenium-containing device combined with ascorbate oxidase.

FIGS. 54A, 54B and 55 show embodiments of a vitamin C biosensor. FIGS. 54A and 54B show the structure of an embodiment of a vitamin C biosensor containing a pH sensing film and an ascorbate oxidase film in an 1×2 array. FIG. 54A is a cross-section, and FIG. 54B is a front view. FIG. 55 shows a cross section of another embodiment of the vitamin C biosensor. The pH sensing unit 502 and vitamin C sensing unit 503 are disposed on a silicon substrate 501. The two sensing units both have ruthenium oxide or ruthenium nitride film 504. Ascorbate oxidase 505 is immobilized on the ruthenium oxide or ruthenium nitride film 504 of the vitamin C biosensor by GPTS 507. The two sensing units are connected to the MOSFET by a metal conductive wire 508. In addition, the sensing units are packed with epoxy 506.

In an embodiment of a biosensor, the sensitivity at different temperature can be obtained by current-voltage (I-V) curves. The temperature coefficient of the ruthenium oxide or ruthenium nitride film can then be obtained and the pH ion concentration of the solution calculated by the temperature coefficient. In addition, the drift value of the embodiment of the biosensor can be measured and accurate output of the biosensor can be obtained by reverse compensatory adjustment. Moreover, the hysteresis value of the embodiment of the biosensor can be measured and the accurate output of the biosensor also obtained by reverse compensatory adjustment.

It was experimentally proved that the embodiment of the vitamin C biosensor with ascorbate oxidase immobilized on the ruthenium oxide film by GPTS can detect the concentration of vitamin C.

For the embodiment of the biosensor, optimum conditions for RF sputtering follow the best sputtering base pressure, the best sputtering power, the best sputtering gas flux, and the best sputtering working pressure.

Figure 2:
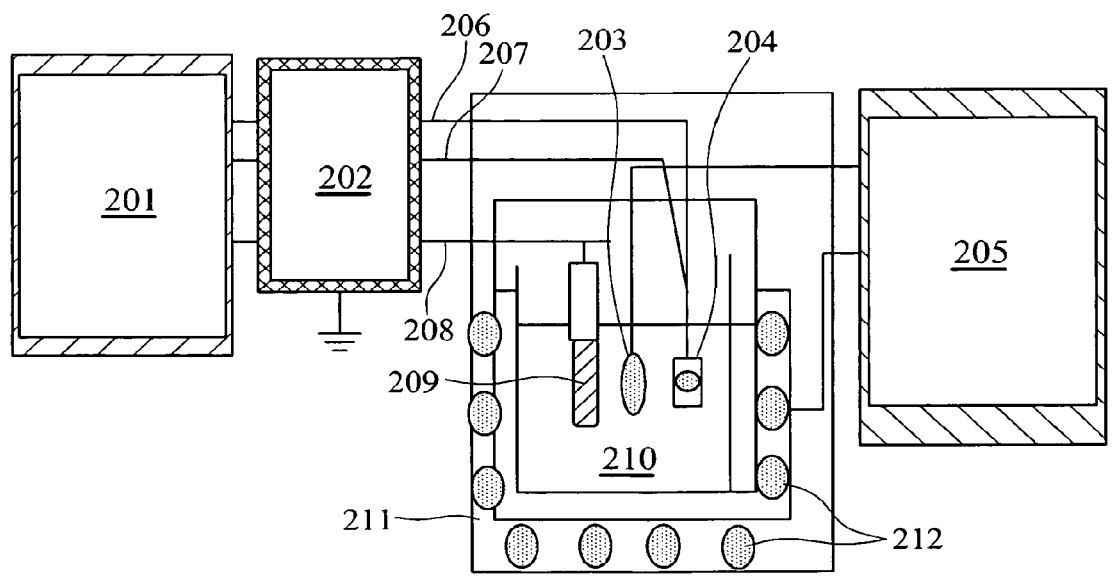
FIG. 2 shows a current-voltage measuring system for the measurement of sensitivity of an embodiment of a biosensor.
Figure 4:
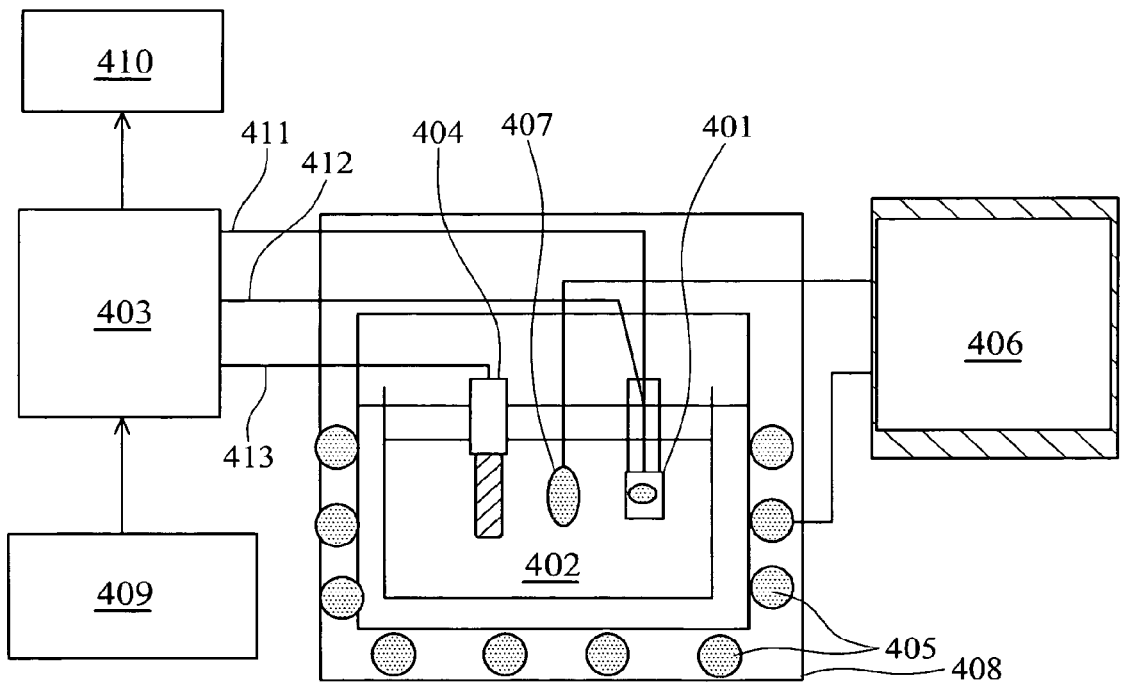
FIG. 4 shows a current-voltage measuring system for the measurement of sensitivity of an embodiment of a biosensor.

The hysteresis width of an embodiment of a ruthenium-containing sensing film can be measured by the measuring system as shown in FIG. 4. The current-voltage measuring system as shown in FIG. 4 can be used to obtain an output response curve. The conditions are as follow: $V_{DS}$=0.2 V and $I_D$=200 μA. The results are recorded each minute by a voltage-time recorder. As for the measurement of the drift value, the sensing unit can be immersed in a standard solution at a fixed temperature controlled by the temperature controller. The whole measuring system can be placed in a dark box to eliminate light interference. The measuring system is a current-voltage measuring system as shown in FIG. 2. The drain current $I_D$ and the drain/source voltage $V_{DS}$ are both fixed and the measurement can be returned to the source voltage $V_s$. The obtained sensing signal is converted to a voltage output signal. The output signals are observed for a long period and the drift value can be obtained. The hysteresis width is the voltage differences between the first and the last pH values.

To obtain the hysteresis value of the embodiment of the ruthenium oxide device or ruthenium nitride device, a loop of pH 5~pH 1~pH 5~pH 9~pH 5 is used. Measurement is started at pH 5, and the result of each pH unit is measured for 1 minute. Each measurement only changes one pH unit. The entire loop has seventeen points and the loop time is 1020 seconds, i.e. 17 minutes. The measurements for 2 and 4 minutes are also detected. The loop time for 2 and 4 minutes is 2040 and 4080 second respectively.

In an embodiment of a vitamin C biosensor, ascorbate oxidase is immobilized on the ruthenium-containing film by 3-glycidoxypropyltrimethoxysilane (GPTS). The vitamin C biosensor is detected in 5, 10, 15, 20, 25, 30, 35, 40, 45, and 50 mM of vitamin C solution. The initial measurement is performed in a buffer solution for 100 seconds. When the signal is stable, the vitamin C biosensor is applied to the test solution for 300 seconds.

Practical examples are described herein.

EXAMPLE

The examples illustrate the preparation of an embodiment of a ruthenium oxide or nitride film, application of the prepared film in ion sensitive electrode, and analysis of the electrode for temperature effect, enzyme property, response time, drift effect, and hysteresis effect. These results can be used for the development of micro-electro-mechanical systems. The conditions for the preparation, measurement, the coefficient, and the device disclosed hereafter are for the purpose of illustrating preferred embodiments of the invention only and not for the purpose of limiting same.

Example 1

Preparation of a Ruthenium-Containing Sensing Film and Design of a Measurement System Using the Same A silicon substrate was cut to 1 cm×1 cm. The silicon dioxide naturally formed on the surface of the substrate was removed by immersing the substrate in a hydrofluoric acid (HF) solution with a ratio of HF and deionized water at 1:50 for 10 minutes. The substrate was then washed with deionized water. The substrate was placed in a sputtering chamber. The working pressure of the reaction chamber was maintained at $2\times10^{-6}$ torr. For ruthenium oxide film, the flow rate of argon was 40 sccm, and that of oxygen was 10 sccm. Ten minutes pre-sputtering was performed at an initial deposition power of 70 W to remove oxides and contaminants from the surface of the ruthenium target. The deposition power was raised to 100 W for sputtering. During the one-hour sputtering, the pressure was maintained at $10\times40^{-3}$ torr. The rotation rate was 10 cpm with a rotating holder to ensure even deposition. Ruthenium oxide film was formed on the silicon substrate, and the sensing unit deposited with a ruthenium oxide film was obtained.

The sensing unit was covered by epoxy resin, exposing partial ruthenium oxide film to form a sensing window. The sensing unit was connected with a gate of a MOSFET by an aluminum wire. The prepared sensing film was cut to 1.5 cm×1.5 cm and washed by deionized water in an ultrasound cleaner. An aluminum wire was fixed to the sensing film by Ag paste and the sensing unit baked at 120° C. for ten minutes. Epoxy resin was applied to the sensing unit and the sensing unit was baked again at 120° C. for 20 minutes. The aluminum wire was passed through a capillary and the entire sensing unit was packaged with epoxy resin to leave a window of 2 mm×2 mm. The sensing unit was then baked at 120° C. for 20~25 minutes.

The wiring structure of the device is shown in FIG. 3 and the current-voltage measuring system in FIG. 2. The sensing unit 204 and an Ag/AgCl reference electrode 209 were immersed in a test solution 210 which was placed in a dark box 211. The wires connected to the source 207 and the drain 206 of a commercialized IC(CD4007UB) and the reference electrode 208 were linked to a testing end 202 which links to a semiconductor characteristic instrument Keithley 236 source measure unit 201. The wire connected to the gate of the commercialized IC was linked to the sensing unit 204. Three Keithly 236s were applied where the first was connected to the source/drain of the IC to provide a suitable bias voltage, the second to the reference electrode, and the third to the drain. The pH-ISFET was regarded as an n-type MOSFET. The temperature of the solution 210 was controlled by a PID temperature controller 205.

The optimal pH range of the ruthenium oxide film was tested from pH 1 to pH 12. For the measurement of a wide range of pH value, the ruthenium nitride film was prepared as described below.

A silicon substrate was cut to 1 cm×1 cm. The silicon dioxide naturally formed on the surface of the substrate was removed by immersing the substrate in a hydrofluoric acid (HF) solution with a ratio of HF and deionized water at 1:50 for 10 minutes. The substrate was then washed with deionized water. The substrate was placed in a sputtering chamber. The working pressure of the reaction chamber was maintained at $2\times10^{-6}$ torr. The flow rate of argon was 15 sccm, and that of nitrogen was 30 sccm. Ten minutes pre-sputtering was performed at an initial deposition power of 70 W to remove oxides and contaminants from the surface of the ruthenium target. The deposition power was raised to 100 W for sputtering. During the one-hour sputtering, the pressure was maintained at $10\times10^{-3}$ torr. The rotation rate was 10 cpm with a rotating holder. Ruthenium nitride film was formed on the silicon substrate, and the sensing unit deposited with a ruthenium nitride film was obtained. The sensing unit was covered by epoxy resin, exposing partial ruthenium oxide film to form a sensing window of 2 mm×2 mm. The sensing unit was connected with a gate of a MOSFET by an aluminum wire. Epoxy resin packaging was performed as described. The wiring structure of the device is shown in FIG. 3 and the current-voltage measuring system in FIG. 2.

Example 2

Preliminary Analysis of the Ruthenium-Containing Biosensor

Figure 5:
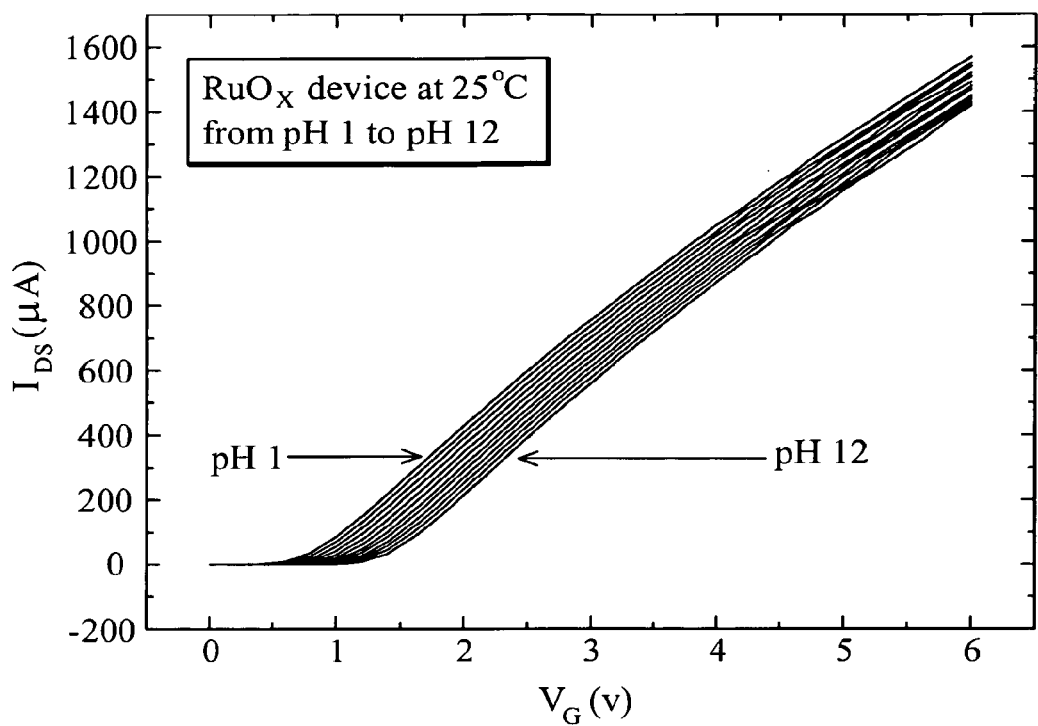
FIG. 5 shows a gate voltage-pH curve of an embodiment of a biosensor containing $RuO_x$ film at various pH values at 25° C.
Figure 6:
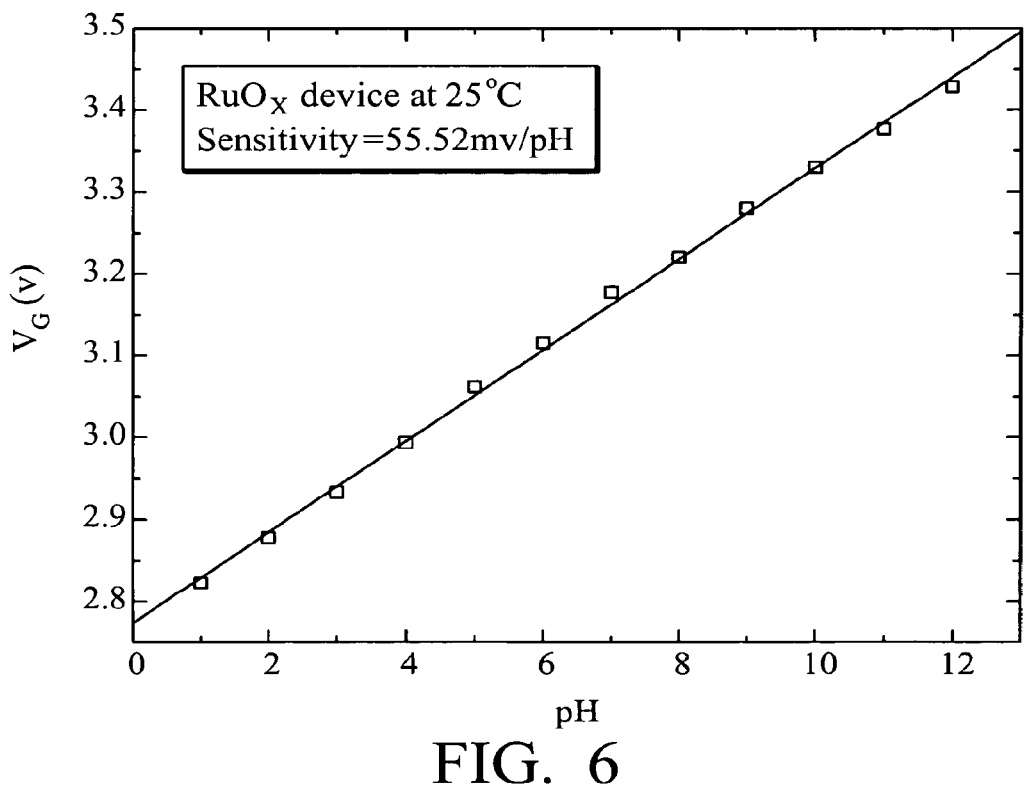
FIG. 6 shows a sensitivity curve of an embodiment of a biosensor containing $RuO_x$ film prepared by a preferred sputtering condition at 25° C.
Figure 7:
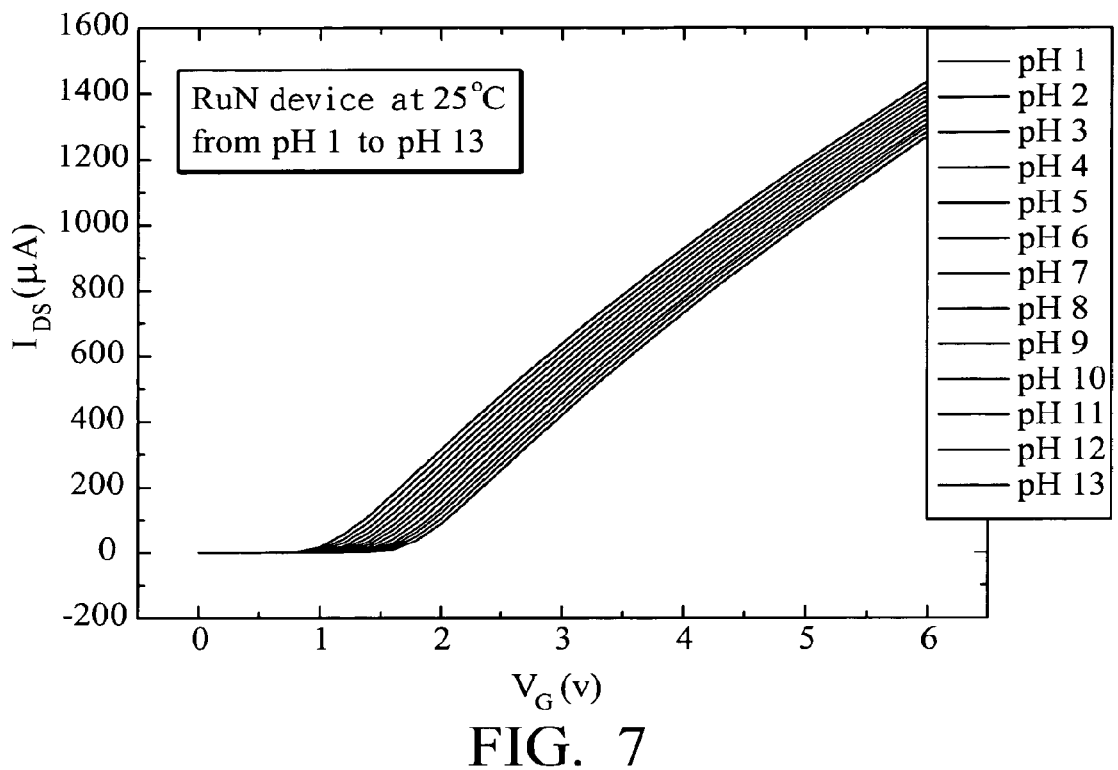
FIG. 7 shows a gate voltage-pH curve of an embodiment of a biosensor containing RuN film at various pH values at 25° C.
Figure 8:
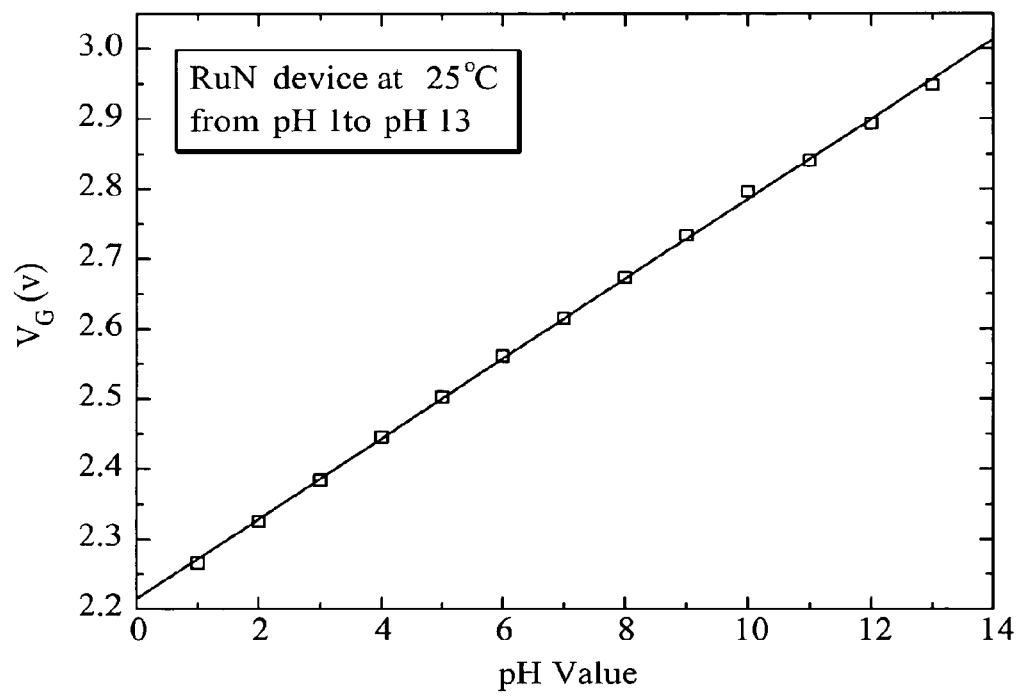
FIG. 8 shows a sensitivity curve (PH-$V_G$ curve) of an embodiment of a biosensor containing RuN film prepared by a preferred sputtering condition at 25° C.

During sputtering, the optimum condition for the ruthenium oxide or ruthenium nitride film was obtained using the I-V measurement system shown in FIG. 2. The measuring results of the ruthenium oxide film are shown in FIG. 5 and the pH of the ruthenium oxide film ranged from pH 1 to pH 12. The results were converted to the relationship of pH and $V_G$ by Origin 6.1 software as shown in FIG. 6, and the sensitivity of the ruthenium oxide film prepared by the optimal sputtering condition was 55.52 mV/pH at 25° C. The I-V measurement results on an enlarged scale showed an ideal linearity with no leakage or noise at the initial voltage. The results of different pH had equidistance, indicating the selectivity to different pH values was good. The measurement results of the ruthenium nitride film are shown in FIG. 7 with the pH measurement of the ruthenium nitride film ranged from pH 1 to pH 13. The results were converted to the relationship of pH and $V_G$ by Origin 6.1 software as shown in FIG. 8, and the sensitivity of the ruthenium nitride film prepared by the optimal sputtering condition was 57.05 mV/pH at 25° C. It should be noted that the results of pH 10 and pH 11 may overlap as the device oxidized with time. The I-V measurement results on an enlarged scale showed an ideal linearity with no leakage or noise at the initial voltage.

The results of the ruthenium oxide and ruthenium nitride films are listed in Table 1.

TABLE 1

Results of the sensitivity in average (unit: mV/pH)

| Times | RuN film | $RuO_X$ film |
|---|---|---|
| $1^{st}$ | 57.05 | 55.52 |
| $2^{nd}$ | 58.18 | 56.34 |
| $3^{rd}$ | 58.01 | 56.02 |
| $4^{th}$ | 58.62 | 55.96 |
| $5^{th}$ | 59.02 | 56.62 |
| $6^{th}$ | 58.34 | 56.73 |
| $7^{th}$ | 58.96 | 55.68 |
| $8^{th}$ | 59.58 | 56.06 |
| $9^{th}$ | 57.69 | 56.68 |
| $10^{th}$ | 58.76 | 55.92 |
| $11^{th}$ | 58.91 | 56.31 |
| $12^{th}$ | 59.06 | 56.43 |
| Sensitivity in average | 58.52 | 56.19 |

Example 3

Characteristic Analysis of the Ruthenium-Containing Biosensor

To further understand the characteristics of the ruthenium-containing biosensor, the following analysis was performed.

Figure 9:
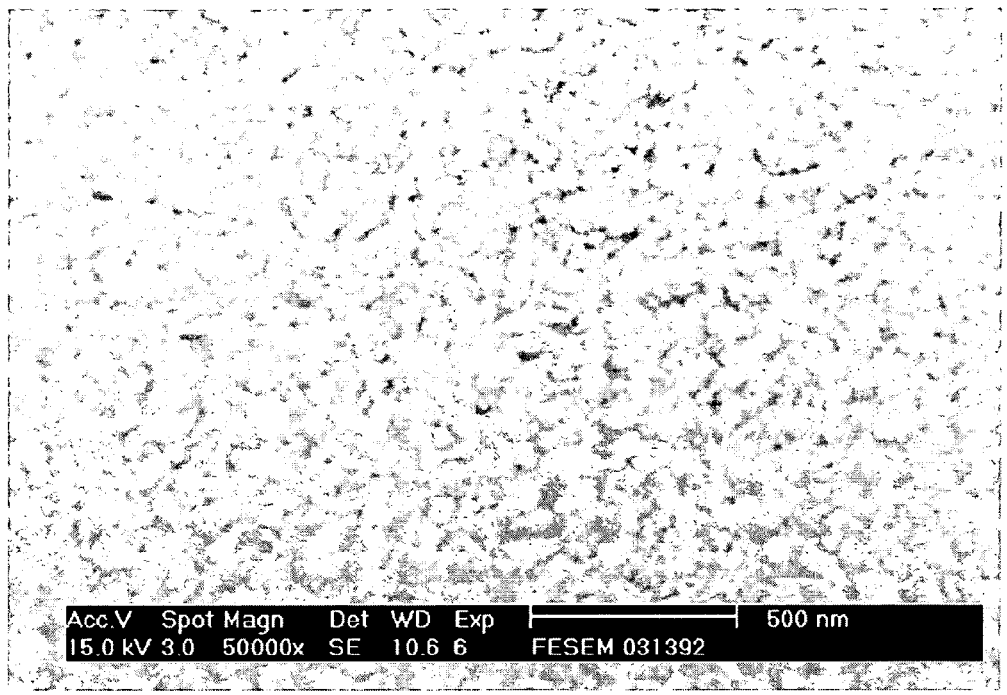
FIG. 9 is a front view of a ruthenium oxide film under SEM. 50,000×.
Figure 10:
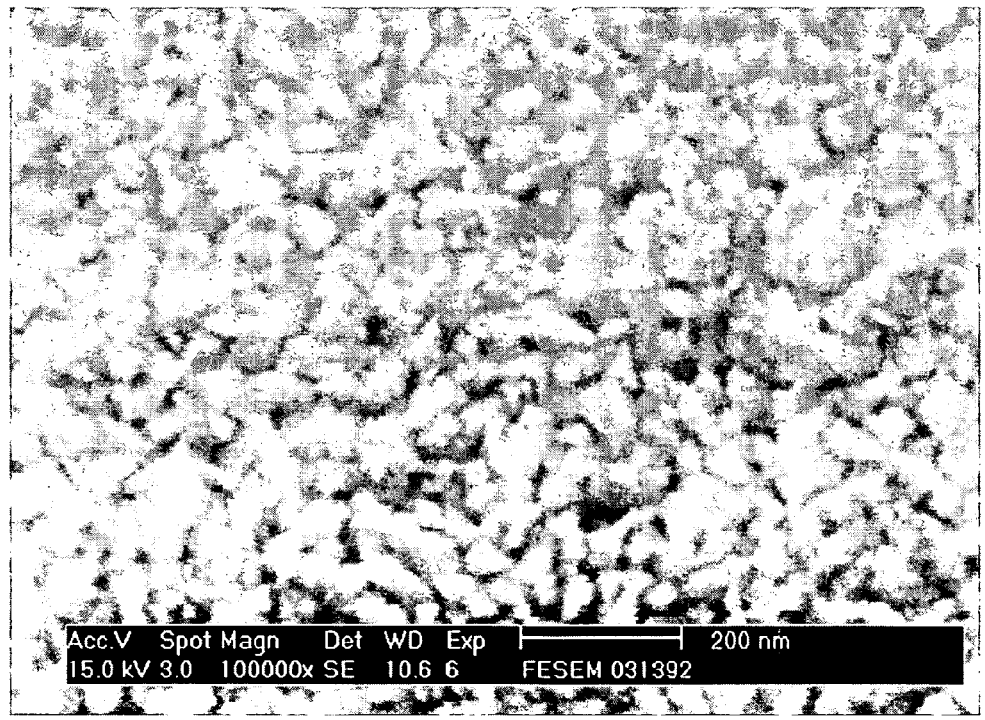
FIG. 10 is a front view of a ruthenium oxide film under SEM. 100,000×.
Figure 11:
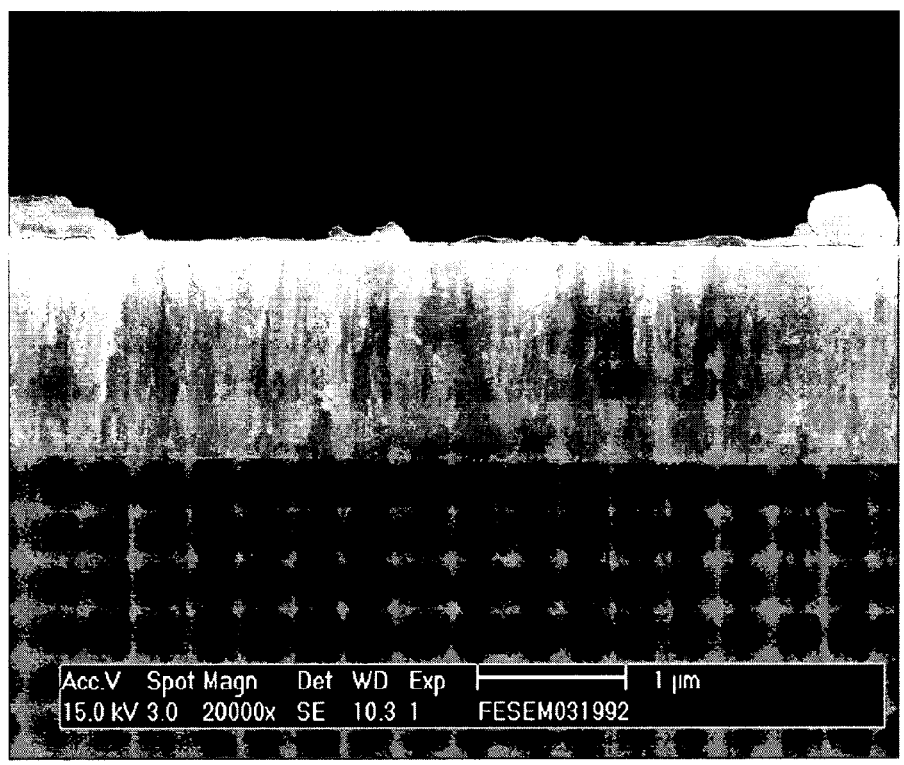
FIG. 11 is a cross section of a ruthenium oxide film under SEM. 20,000×. Thickness=1.67 μm.
Figure 12:
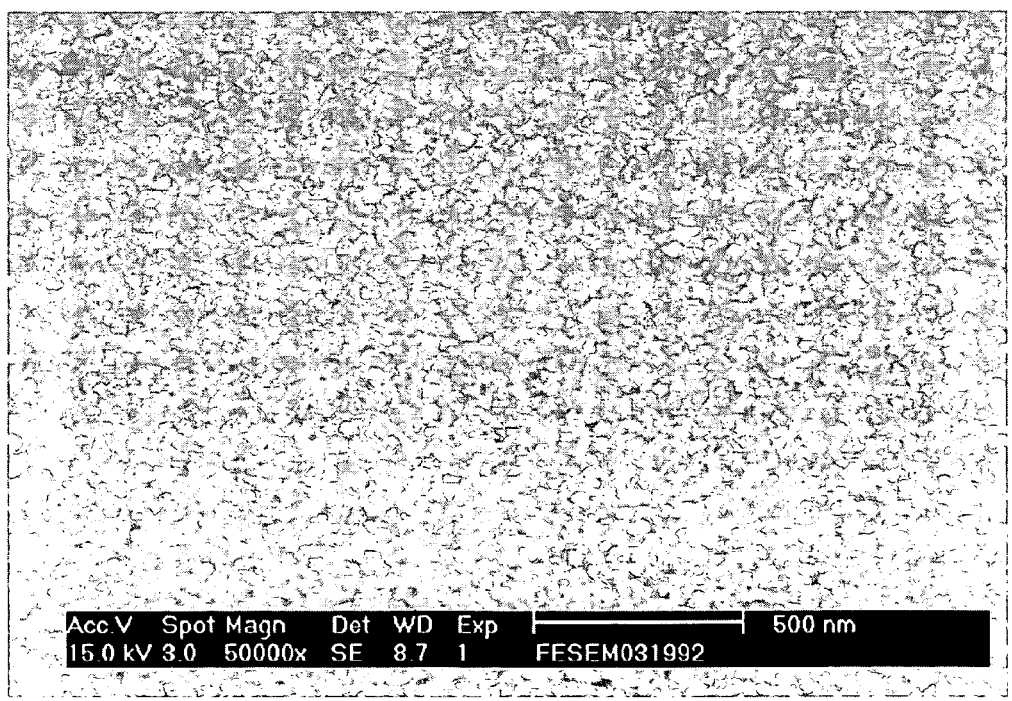
FIG. 12 is a front view of a ruthenium oxide film under SEM. 50,000×.
Figure 13:
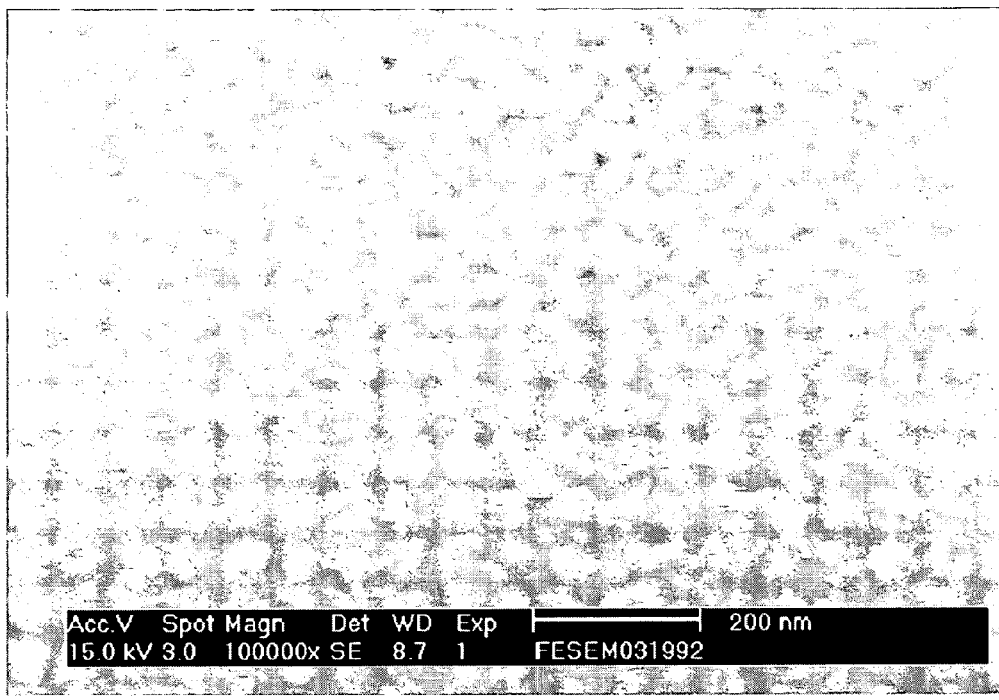
FIG. 13 is a front view of a ruthenium oxide film under SEM. 100,000×.
Figure 14:
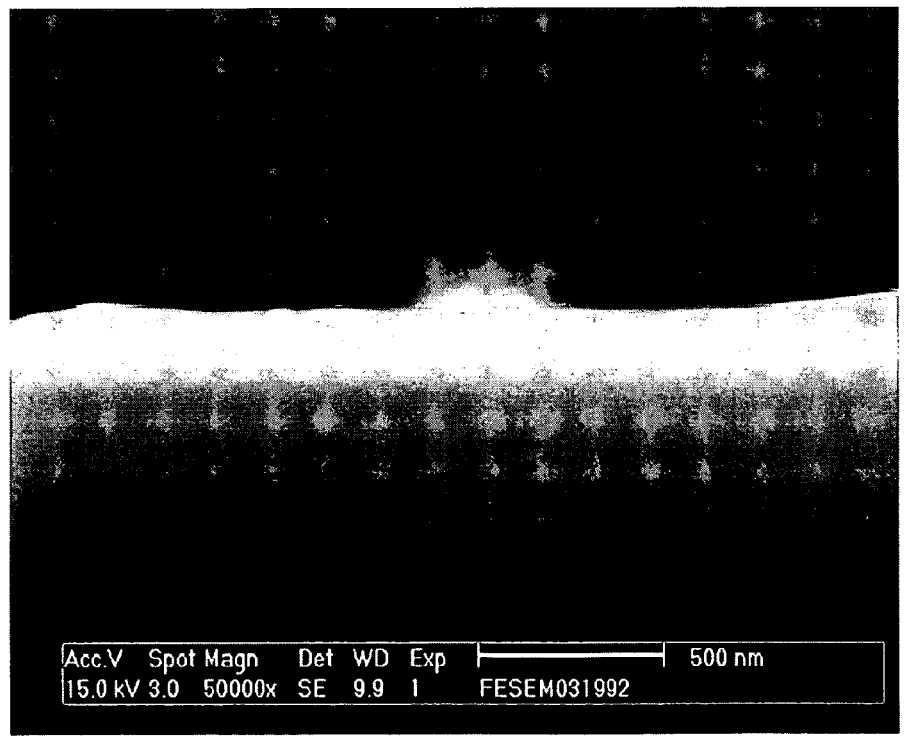
FIG. 14 is a cross section of a ruthenium oxide film under SEM. 50,000×. Thickness=164 nm.
Figure 15:
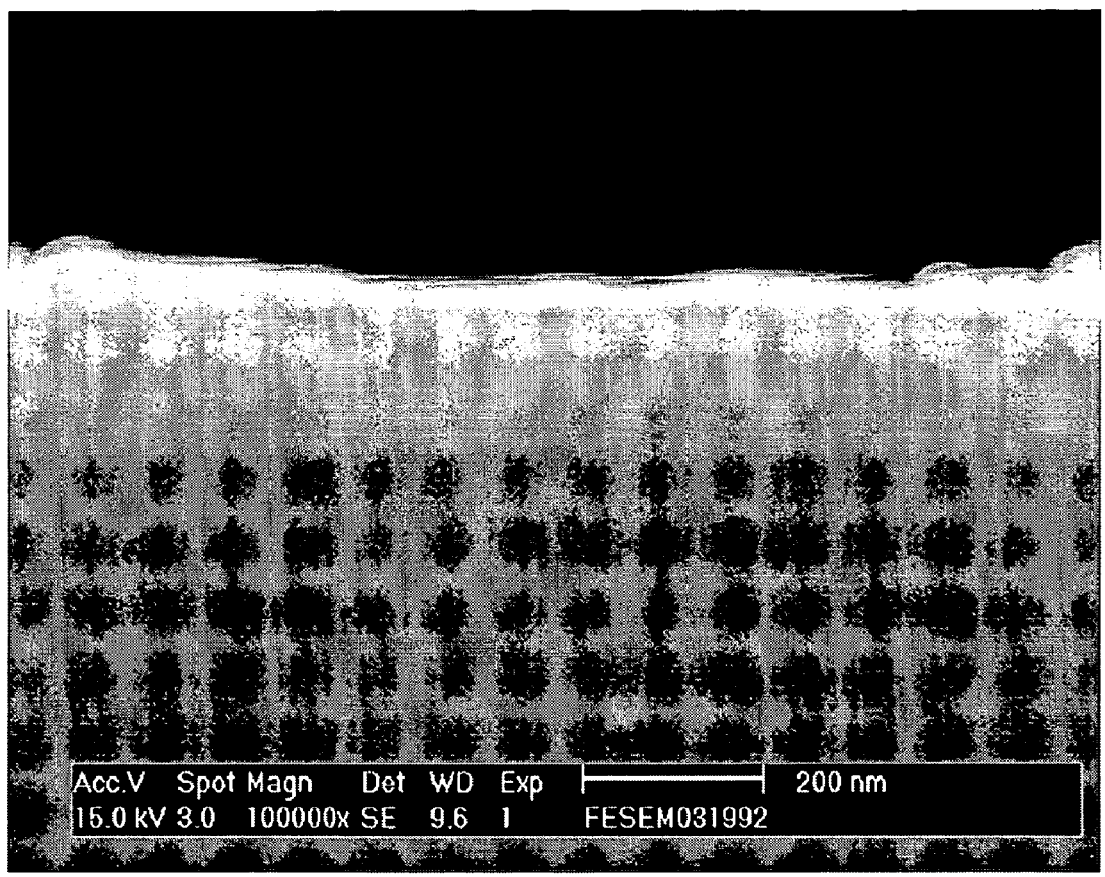
FIG. 15 is a cross section of a ruthenium oxide film under SEM. 100,000×. Thickness=164 nm.
Figure 16:
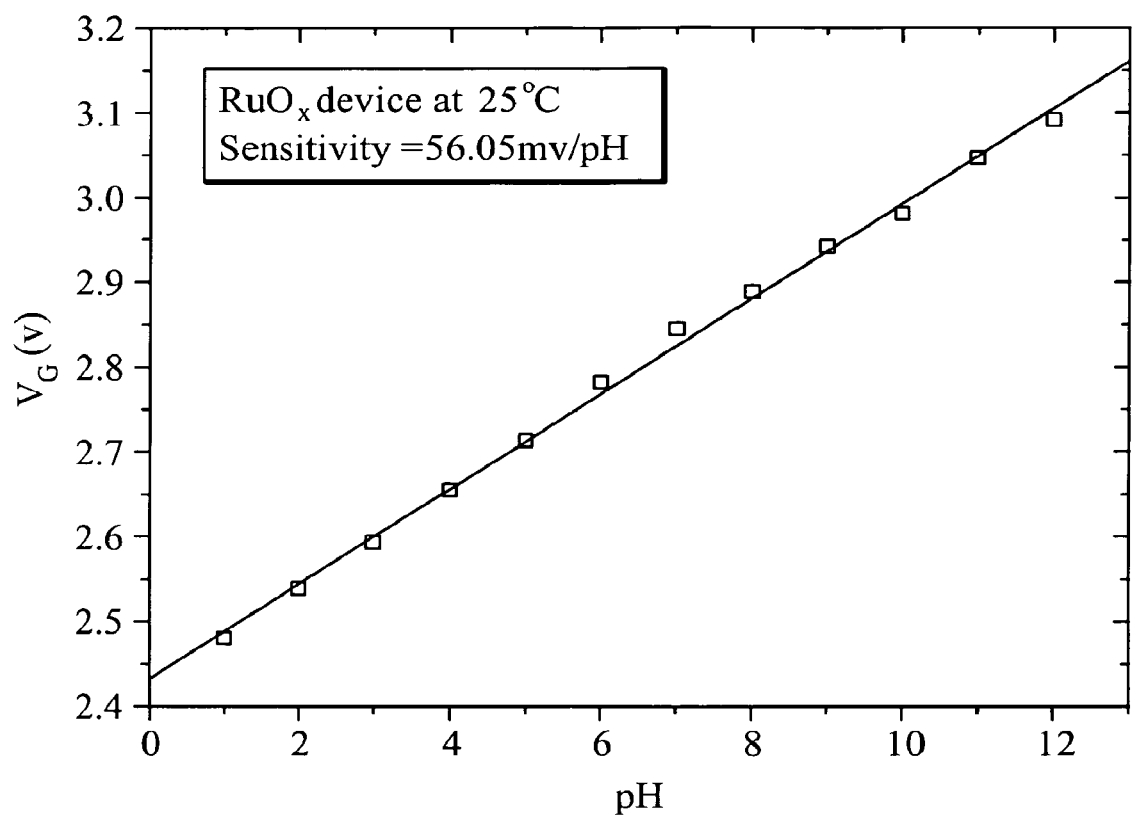
FIG. 16 is a sensitivity curve (PH-$V_G$ curve) of an embodiment of a biosensor containing $RuO_x$ film pH 1-pH 12.
Figure 17:
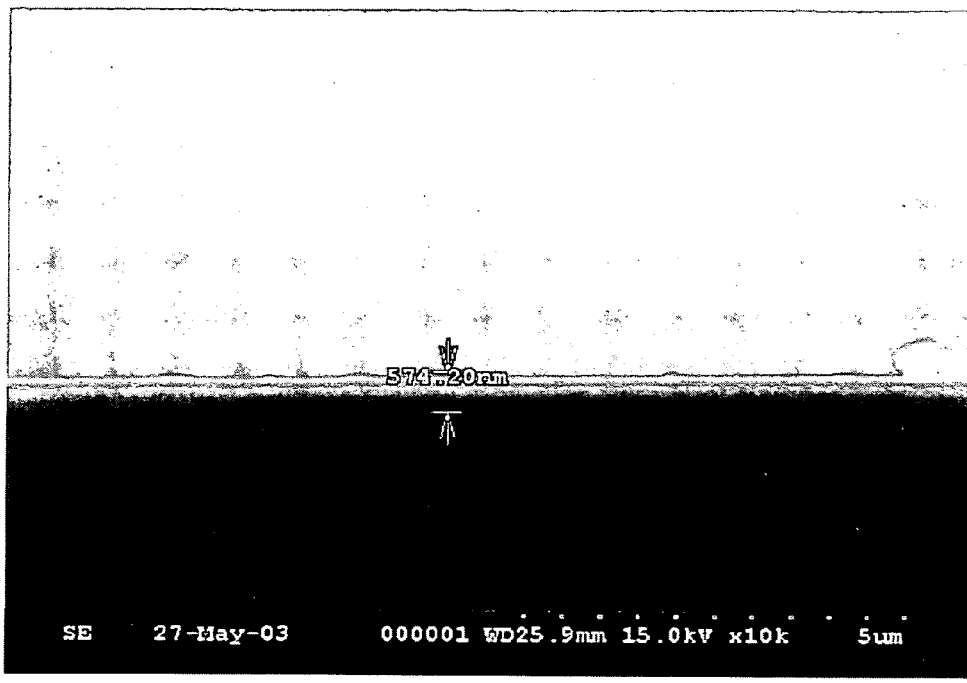
FIG. 17 is a cross section of an embodiment of a ruthenium nitride film under SEM. 10000×. Thickness=574.2 nm.

A. Scanning Electron Microscopy:

Scanning Electron Microscopy (SEM) JEOL JSM-6330F FESEM was applied for the measurement of the ruthenium oxide film and the results were shown in FIGS. 9~11. FIGS. 9 and 10 show the front views of the ruthenium oxide film at 50,000× and 100,000× respectively. The crystalline phase and structure of the ruthenium oxide was observed. FIG. 11 is a cross section of the ruthenium oxide film at 20,000× with thickness of 1.76 μm. To determine the relationship between the thickness and the sensing response, a ruthenium oxide film prepared with another sputtering coefficient was formed under working pressure maintained at $2\times10^{-6}$ torr, flow rate of argon 40 sccm, and oxygen 10 sccm. Ten minutes pre-sputtering was performed at an initial deposition power of 70 W to remove oxides and contaminants from the surface of the ruthenium target. The deposition power was raised to 100 W for $RuO_x$ sputtering. During the one-hour sputtering, the pressure was maintained at $5.3\times10^{-3}$ torr. The rotation rate was raised to 15 cpm to form an evener surface. The ruthenium oxide film was measured by scanning electron microscope with the results shown in FIGS. 12~15. FIGS. 12 and 13 are front views of the ruthenium oxide film at 50,000× and 100,000× respectively, and FIGS. 14 and 15 are cross sections at 50,000× and 100,000× respectively. Thickness was 164 nm and particle size about 20-50 nm. The sensitivity of such nano-level ruthenium oxide film was 56.05 mV/pH as shown in FIG. 16, indicating thickness and the sensitivity of the ruthenium oxide film have no direct relationship. As for the ruthenium nitride film, the SEM result is shown in FIG. 17 with a thickness of 574.2 nm. To further clarify the relationship between the surface area and sensing response, atomic force microscopy was performed.

B. Atomic Force Microscopy (AFM)

Figure 18:
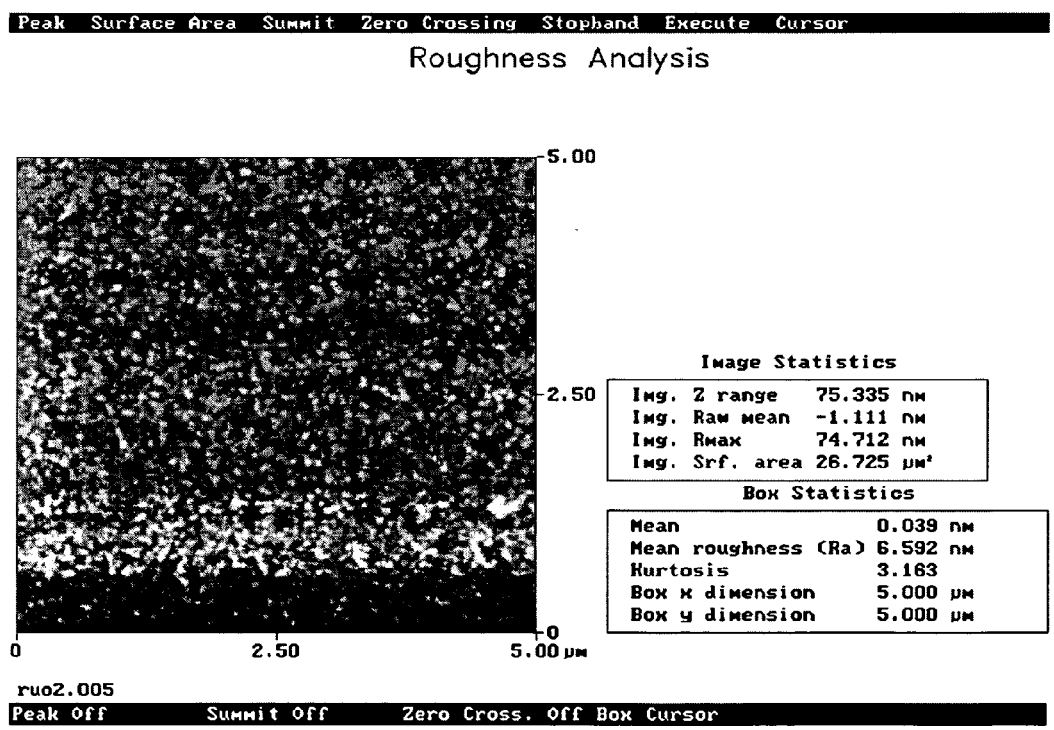
FIG. 18 is a roughness analysis of an embodiment of a ruthenium oxide film under AFM. Thickness=1670 nm.
Figure 19:
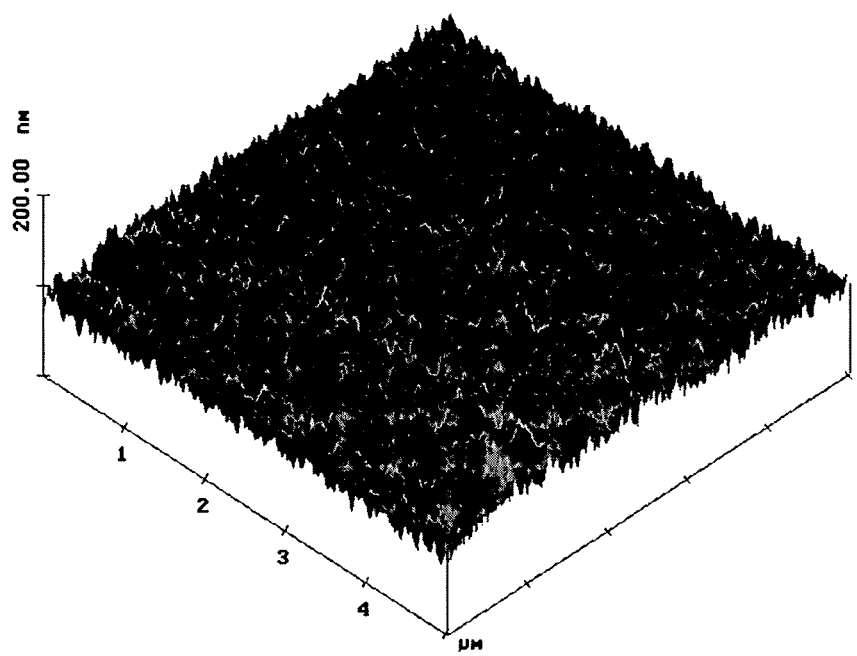
FIG. 19 is a roughness analysis of an embodiment of a ruthenium oxide film under AFM. Thickness=1670 nm.
Figure 20:
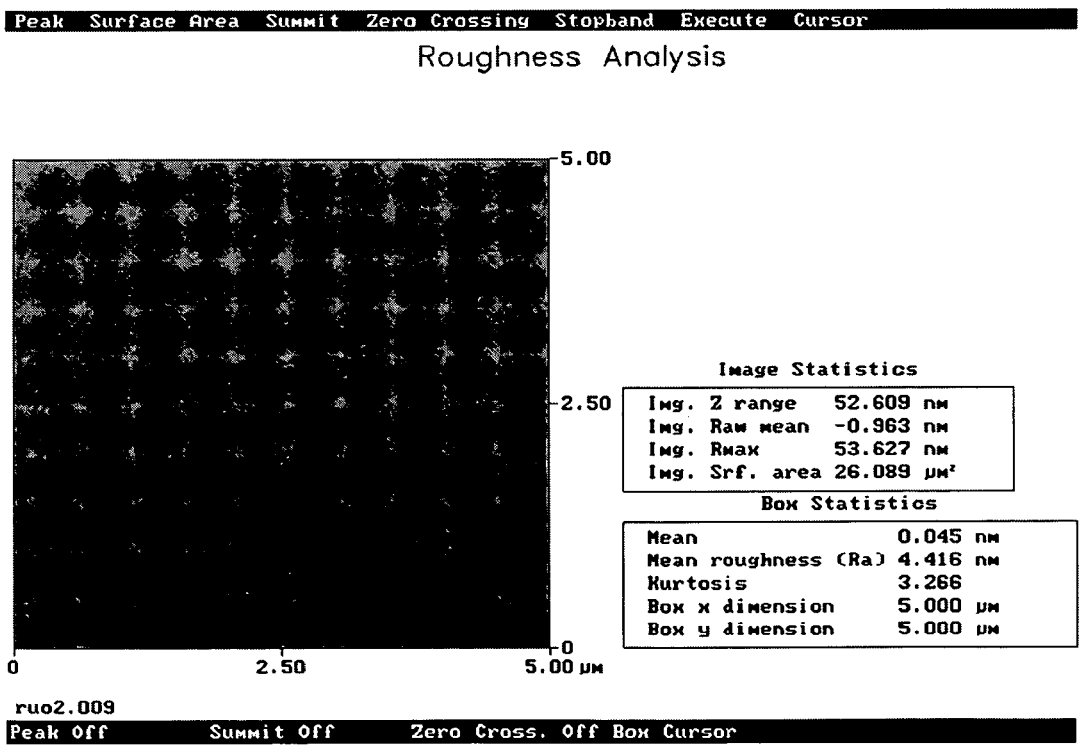
FIG. 20 is a roughness analysis of an embodiment of a ruthenium oxide film under AFM. Thickness=164 nm.
Figure 21:
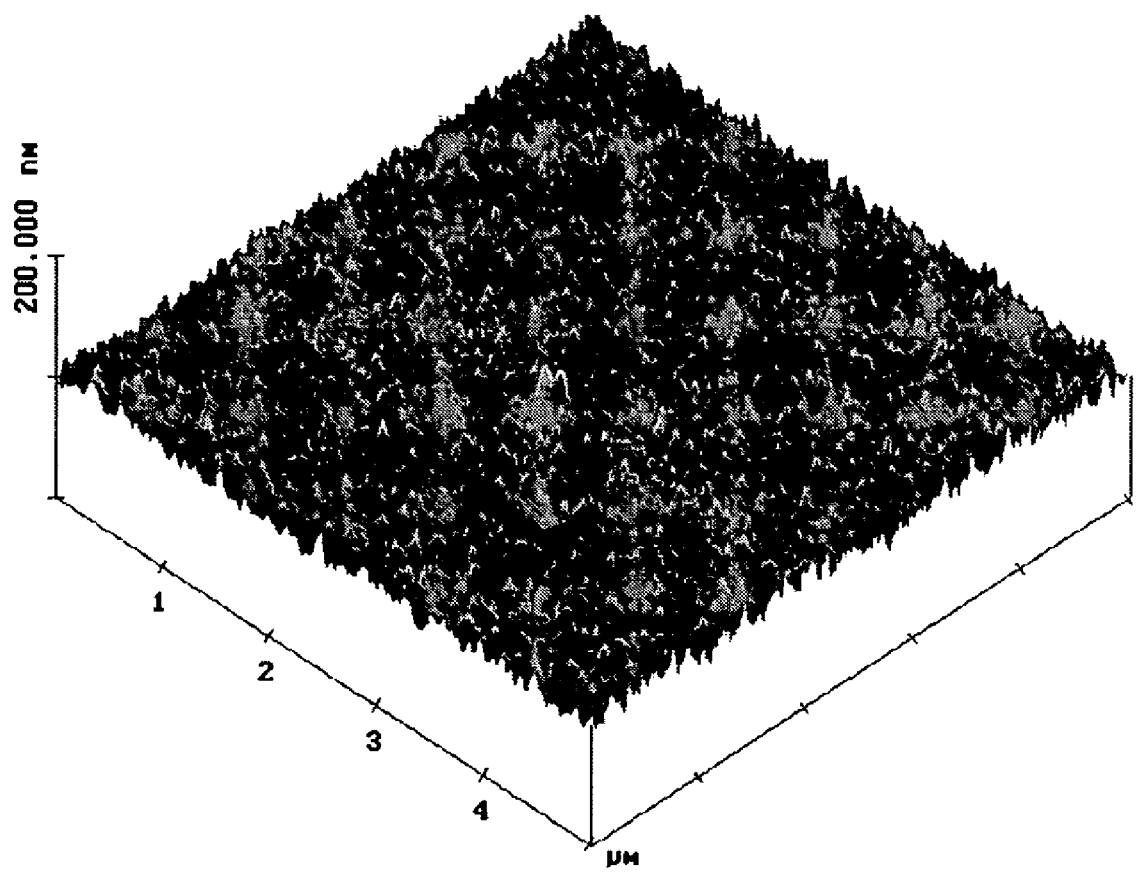
FIG. 21 is a roughness analysis of an embodiment of a ruthenium oxide film under AFM. Thickness=164 nm.

Atomic Force Microscopy (AFM) was performed by Nanoscope III SPM (Scanning Probe Microscope controller, purchased by Digital Instrument (DI)). The undulate surface of the ruthenium oxide with a thickness of 1670 nm is shown in FIGS. 18 and 19. The mean undulation is 0.039 nm, and the mean roughness 6.592 nm. The undulate surface of the ruthenium oxide with a thickness of 164 nm is shown in FIGS. 20 and 21. The mean undulation is 0.045 nm, and the mean roughness 4.416 nm. Since the latter (164 nm in thickness) has a sensitivity of 56.05 mV/pH higher than that of the former which is 1670 nm in thickness and has a sensitivity of 55.52 mV/pH, it confirmed that the mean undulation, not the mean roughness, is related to the sensitivity. The peak structure which increases the porosity and the surface area of the film for redox reaction may facilitate the sensitivity.

C. Electron Spectroscopy for Chemical Analysis (ESCA)

Figure 22:
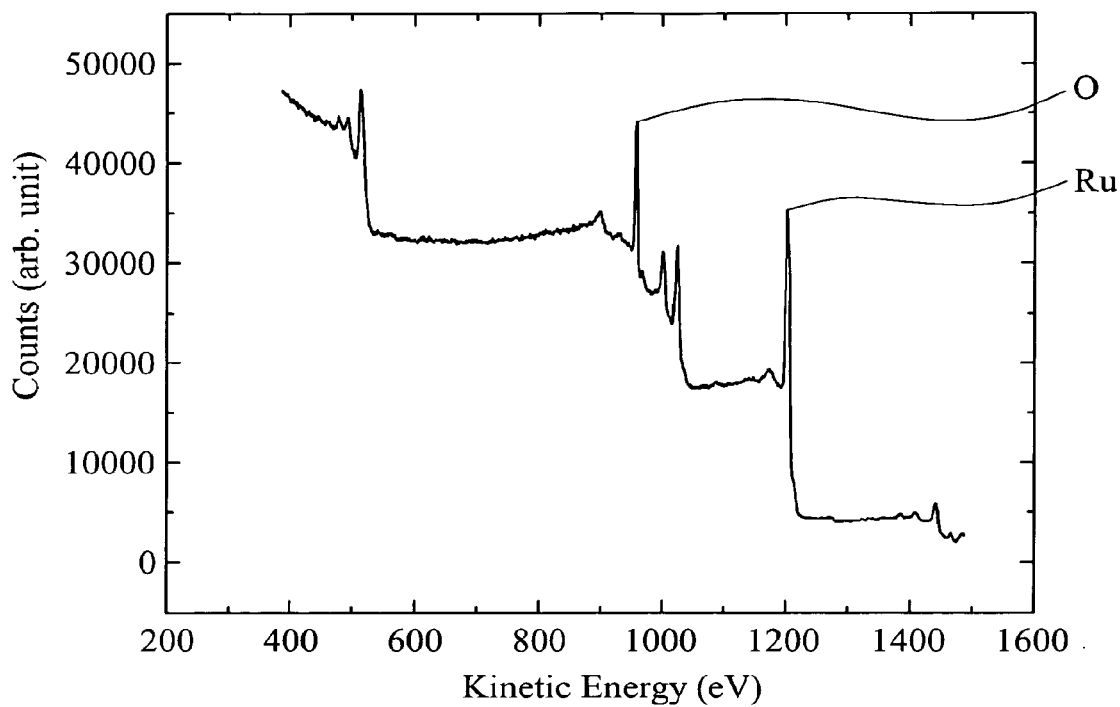
FIG. 22 shows ESCA scan results of an embodiment of a ruthenium oxide film. Thickness=1670 nm.
Figure 23:
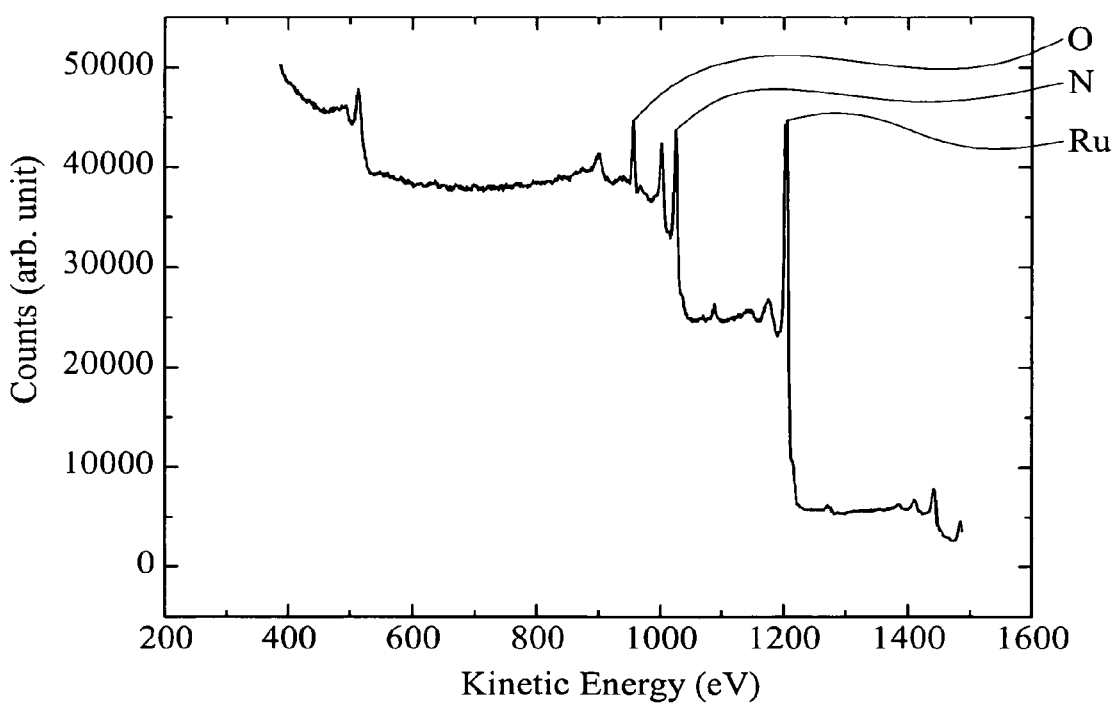
FIG. 23 shows ESCA scan results of an embodiment of a ruthenium nitride film. Thickness=574.2 nm.

Electron Spectroscopy for Chemical Analysis (ESCA) was performed by Fison (VG) ESCA 210, and Mg target was used as X ray source for the qualitative and quantitative analysis. The species and amounts of the surface components can be analyzed by measuring the intensity of the photoelectron. ESCA was applied to determine the atomic species and chemical status of the photoelectron. The results are shown in FIGS. 22 and 23. The analysis results of the components are shown in Table 2. The results indicate that surface components of the ruthenium oxide film are $Ru:O_2=31.19:68.81$ (unit %), and of the ruthenium nitride film $Ru:N:O_2=35.4:31.5:33.1$ (unit %). These results which did not comply with the theoretical results were further confirmed by Energy Dispersive Spectrometer (EDS) as follows.

D. Energy Dispersive Spectrometer (EDS)

Figure 24:
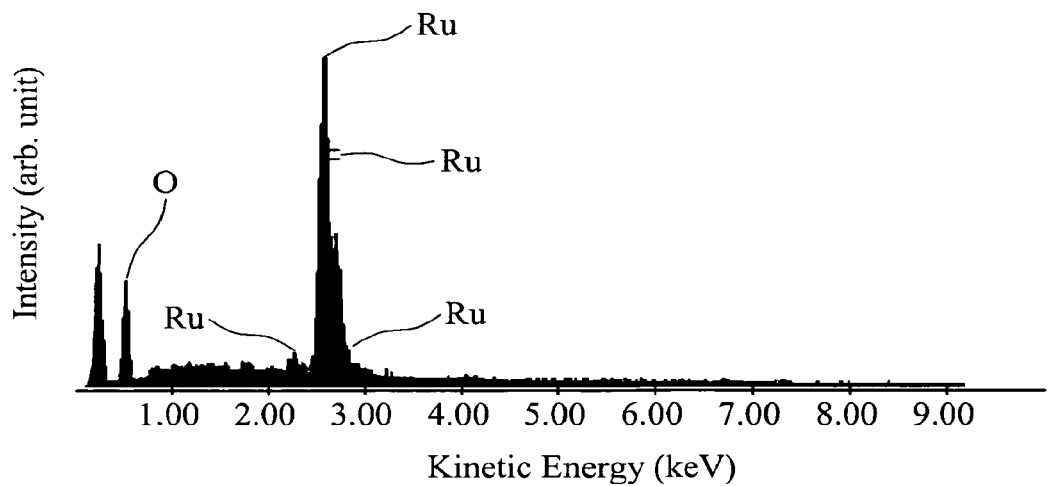
FIG. 24 shows EDS scan results of an embodiment of a ruthenium oxide film. Thickness=1670 nm.

The Energy Dispersive Spectrometer (EDS) used was JEOL JSM-6330F FESEM. The energy dispersive spectrum results showed that the bulk components of the ruthenium oxide film are $Ru:O_2=67.8:32.2$ (unit %), as shown in FIG. 24, and of the ruthenium nitride $Ru:N=53.4:46.6$ (unit %). The component analysis is shown in Table 2. For the understanding of the crystallographic direction of the ruthenium-containing film, X-Ray Diffraction (XRD) was applied as follows.

E. X-Ray Diffraction (XRD)

Figure 25:
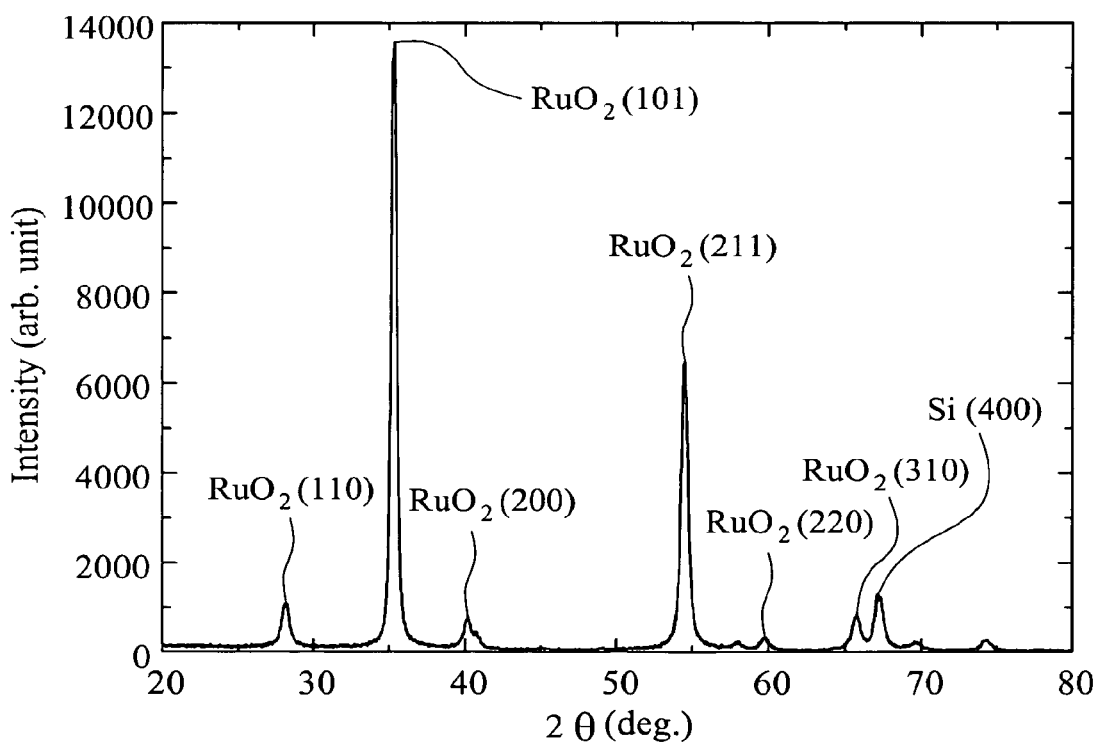
FIG. 25 shows a XRD pattern of an embodiment of a ruthenium oxide film. Thickness=1670 nm.
Figure 26:
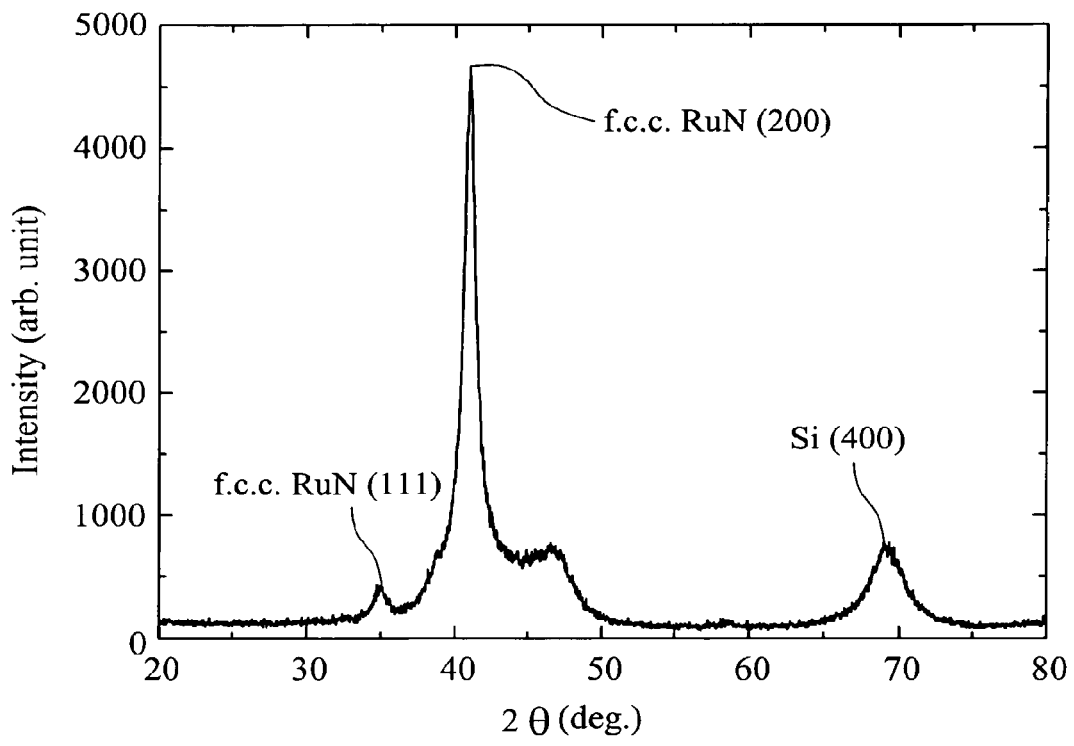
FIG. 26 shows a XRD pattern of an embodiment of a ruthenium nitride film. Thickness=574.2 nm.

X-Ray Diffraction (XRD) was performed by a high resolution X-ray diffractometer Rigaku ATX-E and a wide angle X-ray diffractometer Rigaku D/MAX2500 equipped with X-ray source having high power rotating anode. The wide angle X-ray diffractometer may be used to test glancing incident angle diffraction. The results are shown in FIGS. 25 and 26. FIG. 25 shows the crystallographic direction of ruthenium dioxide, and FIG. 26 shows the crystallographic direction of ruthenium nitride.

F. Resistance Using the Current-Voltage Measurement System

Figure 27:
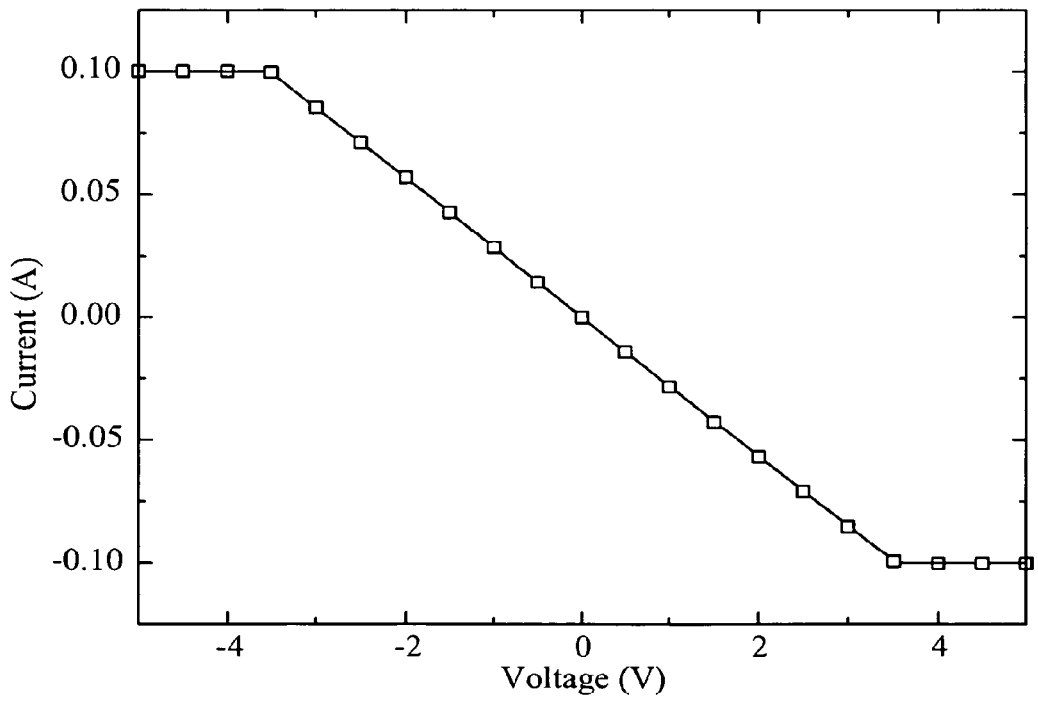
FIG. 27 shows a surface current-voltage curve of an embodiment of a ruthenium oxide film. Area: 0.8 cm×1 cm, thickness=1670 nm.
Figure 28:
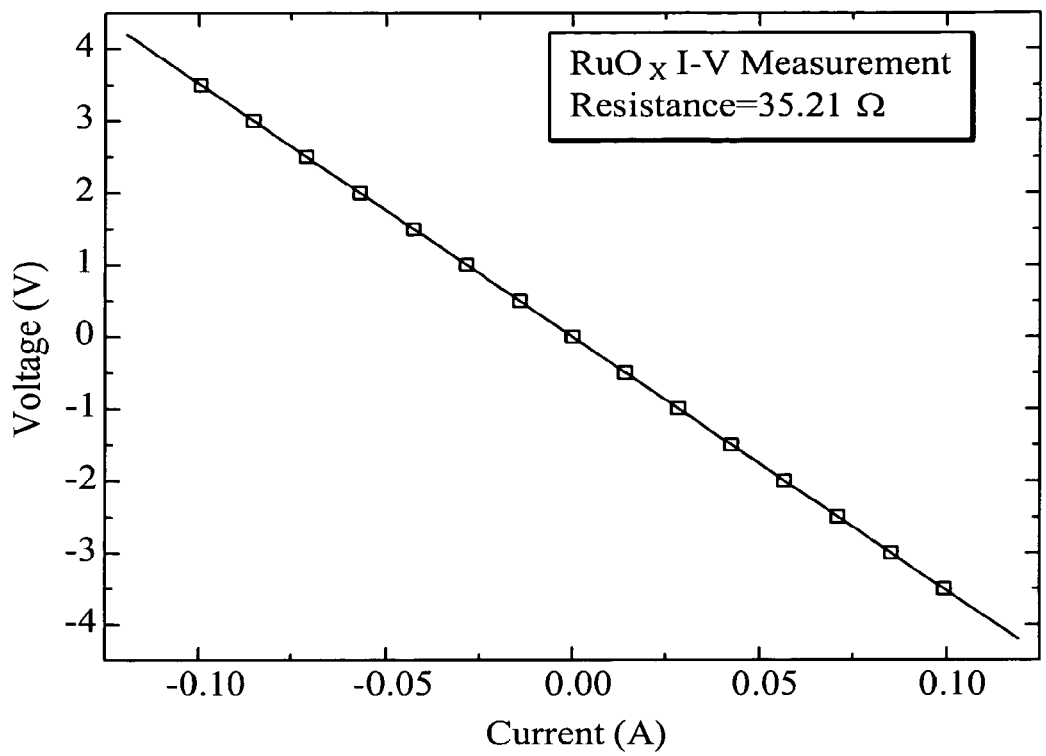
FIG. 28 shows a surface current-voltage curve of an embodiment of a ruthenium oxide film. Resistance rate: $7.746 \times 10^{-5}$ Ω·m.
Figure 29:
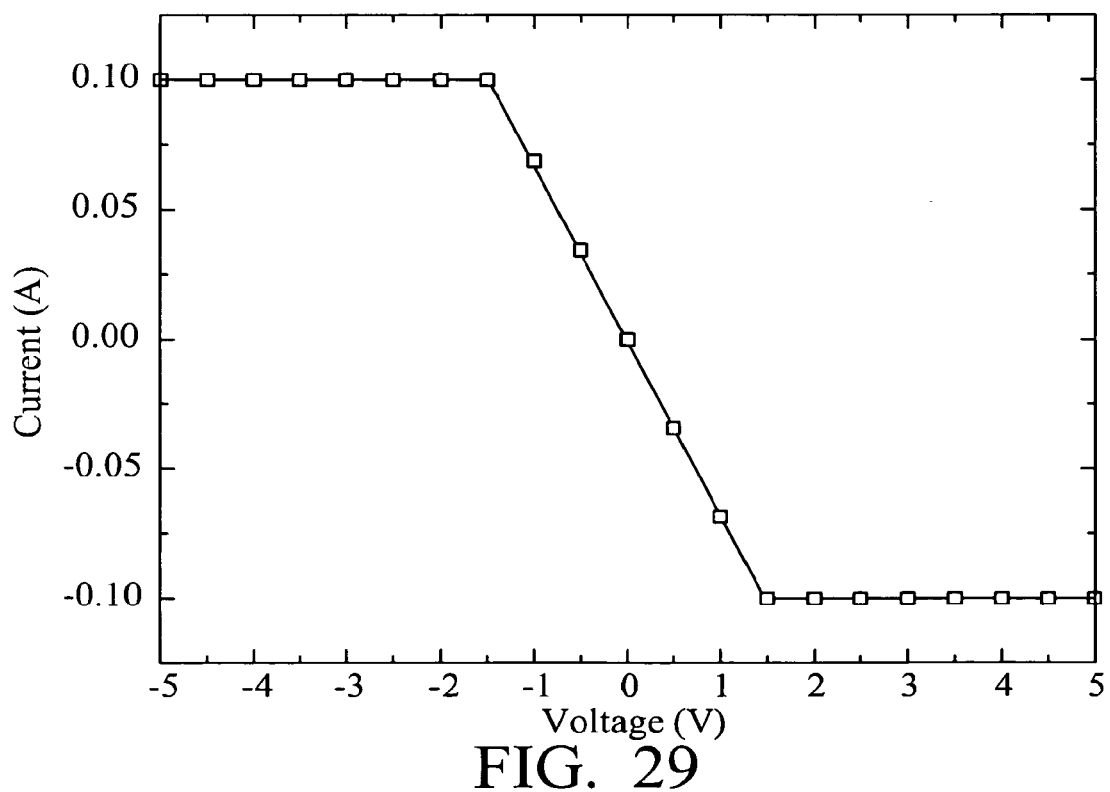
FIG. 29 shows a surface current-voltage curve of an embodiment of a ruthenium nitride film. Area: 1 cm×1 cm, thickness=574.2 nm.
Figure 30:
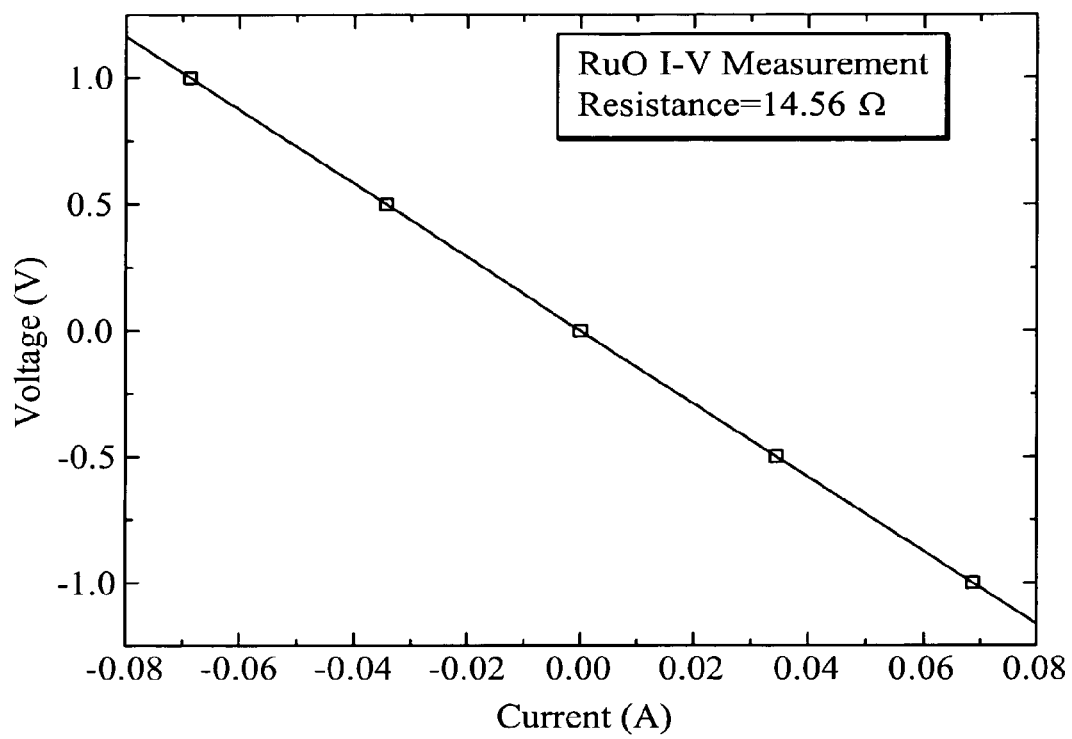
FIG. 30 shows a surface current-voltage curve of an embodiment of a ruthenium oxide film. Resistance rate: $8.96 \times 10^{-6}$ Ω·m.

Resistance of the ruthenium-containing films was measured by the two-probe method of current-voltage (I-V), and the I-V results are shown in FIGS. 27 and 29 and the linear slopes shown in FIGS. 28 and 30 respectively. The resistance of the ruthenium oxide film was $7.746\times10^{-5}$ Ω·m and that of the ruthenium nitride film was $8.96\times10^{-6}$ Ω·m, as listed in Table 2.

TABLE 2

Comparison of the ruthenium oxide and ruthenium nitride films

| Items | Ruthenium oxide film | Ruthenium nitride film | Measurement |
|---|---|---|---|
| Bulk | $Ru_3O$ | $RuN$ | EDS |
| Surface | $RuO_X$ | $RuNO_3$ | ESCA |
| Sputtering ratio (sccm) | $Ar:O_2 = 40:15$ | $Ar:N = 15:30$ | |
| Sputtering time (hour) | 1 | 1 | |
| Sputtering power (W) | 100 | 100 | |
| Mean sensitivity (mV/pH) | 56.19 | 58.52 | I-V |
| Sensitive range | pH 1-12 | pH 1-13 | I-V |
| Thickness (nm) | 1760 | 574.2 | SEM |
| Surface components (%) | $Ru:O_2 = 31.19:68.81$ | $Ru:N:O_2 = 35.4:31.5:33.1$ | ESCA |
| Bulk components (%) | $Ru:O_2 = 67.8:32.2$ | $Ru:N = 53.4:46.6$ | EDS |
| Linearity | good | Good | I-V |
| Leakage | About 0.1 μA | no | I-V |
| Selectivity | Excellent | Excellent | I-V |
| Resistance (Ω · m) | $7.746 \times 10^{-5}$ | $8.96 \times 10^{-6}$ | Two probe method |

According to the results listed in Table 2, the characteristics of the embodiment of the ruthenium-containing film can be concluded as follows.

Figure 31:
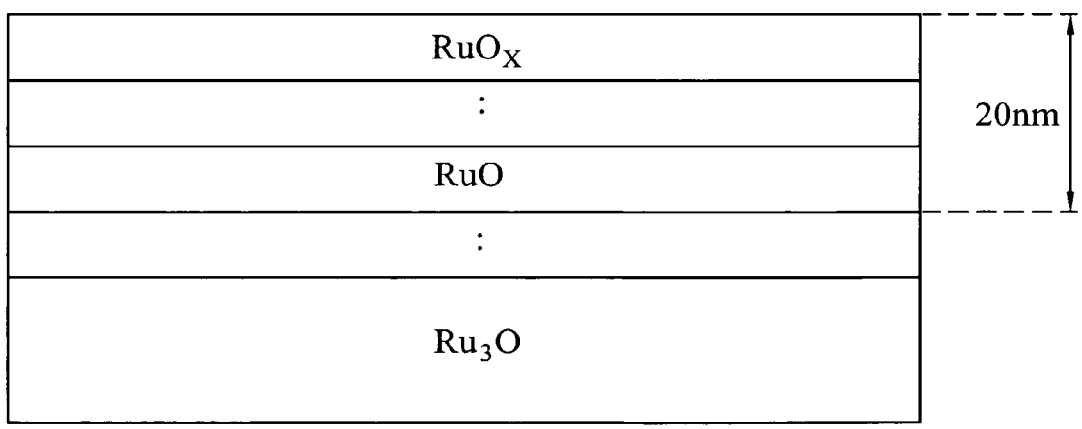
FIG. 31 is a cross section of an embodiment of a ruthenium oxide film.
Figure 32:
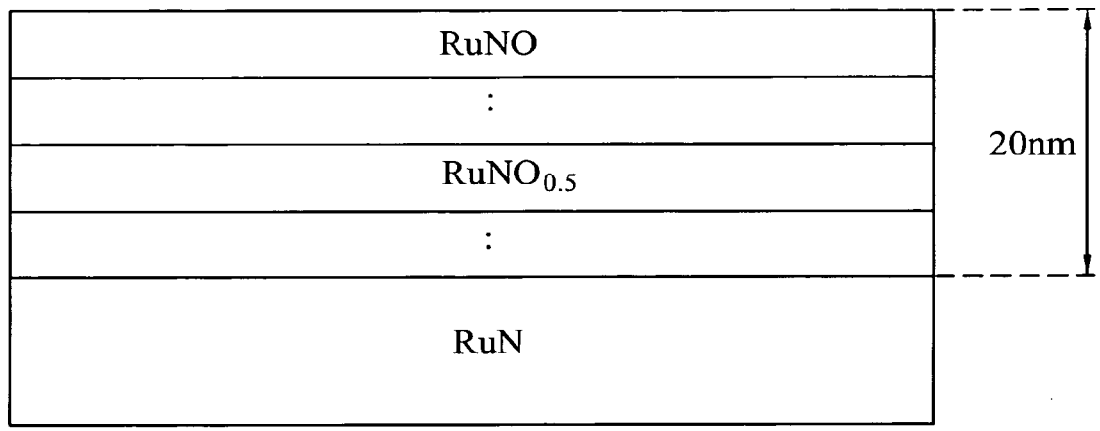
FIG. 32 is a cross section of an embodiment of a ruthenium nitride film.
Figure 33:
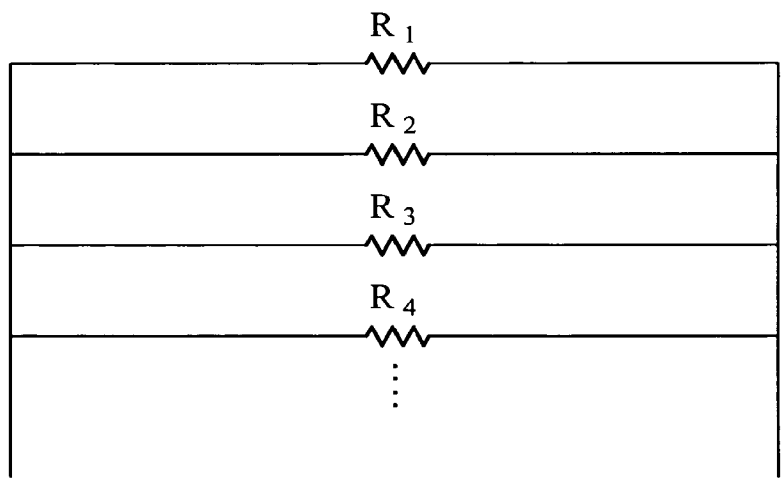
FIG. 33 is a resistance structure of an embodiment of a sensing membrane. $R_{eq} \| R_1 \| R_2 \| R_3 \| \ldots \| R_n$, $R_{eq} = \min\{R_1, R_2, R_3, \ldots R_n\}$.
Figure 34:
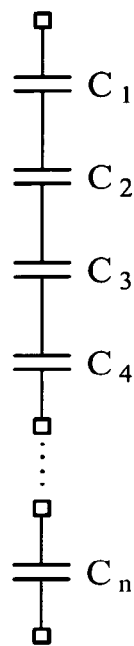
FIG. 34 shows the capacitor structure of an embodiment of a sensing film. $C_{eq} = C_1 + C_2 + C_3 + \ldots + C_n$, $C_{eq} = \min\{C_1, C_2, C_3, \ldots, C_n\}$.

There are two parts of the sensing film, the bulk and the surface. It was found by EDS that the bulk is under 20 nm from the surface of the sensing film and redox reaction is performed on the surface of the sensing film. Resistance is related to both and can be parallel by the multi-layer. Multiple-layers or double layer can be formed according to the sputtering. The final disvacuum step of the preparation of the ruthenium-containing film was performed by air, leading to a multi-layer structure with descending oxygen content from the surface. As a result, the surface is highly oxidized layer with a thickness of less than 20 nm. With the decreased oxygen ratio, the resistance also decreases layer by layer and the bulk becomes a good conductor. The structure of the ruthenium oxide film is shown in FIG. 31, and that of the ruthenium nitride film is shown in FIG. 32. In low frequency measurement, resistors in parallel bring the equivalent resistance value close to the smallest resistance value as shown in FIGS. 33 and 34. FIG. 34 shows capacitors in series bring the equivalent capacity close to the smallest capacity and the delay time (T=RC) is the smallest. According to electrochemical theory, parasitic resistors and parasitic capacitors are of concern in such structure with a thin surface, however, the measurement of the embodiment of the biosensor requires relatively long sampling time and does not have this problem.

Example 4

Sensitivity Analysis of the Ruthenium-Containing Biosensor

A. Temperature Effect

Temperature effect of the ruthenium-containing film was obtained by the measuring system of $I_{DS}$-$V_G$ curve as shown in FIG. 4. Sensitivity of the film was measured at different temperatures. First, the ruthenium-containing biosensor was immersed in different buffer solutions at a fixed temperature for 20 seconds. For ruthenium oxide film, measurement was performed at pH 1 to pH 12, and for ruthenium nitride film, the measurement was performed at pH 1 to pH 13. The curves of drain/source current and gate voltage ($I_{DS}$-$V_G$) were obtained respectively. The temperature of the measuring circumstances was adjusted at 5, 15, 25, 35, 45, 55, 65, and 75° C. by the PID temperature controller and the described measurement procedures were repeated.

The results are shown in Tables 3 and 4.

TABLE 3

Sensitivity of the ruthenium oxide film at various temperatures

| Temperature (° C.) | Sensitivity (mV/pH) |
|---|---|
| 5 | 52.93 |
| 15 | 54.52 |
| 25 | 55.52 |
| 35 | 56.02 |
| 45 | 56.68 |
| 55 | 57.89 |
| 65 | 59.63 |
| 75 | 60.59 |

TABLE 4

Sensitivity of the ruthenium nitride film at various temperatures

| Temperature (° C.) | Sensitivity (mV/pH) |
|---|---|
| 5 | 53.94 |
| 15 | 56.15 |
| 25 | 58.42 |
| 35 | 59.39 |
| 45 | 60.92 |
| 55 | 62.43 |
| 65 | 64.66 |
| 75 | 65.83 |

Figure 35:
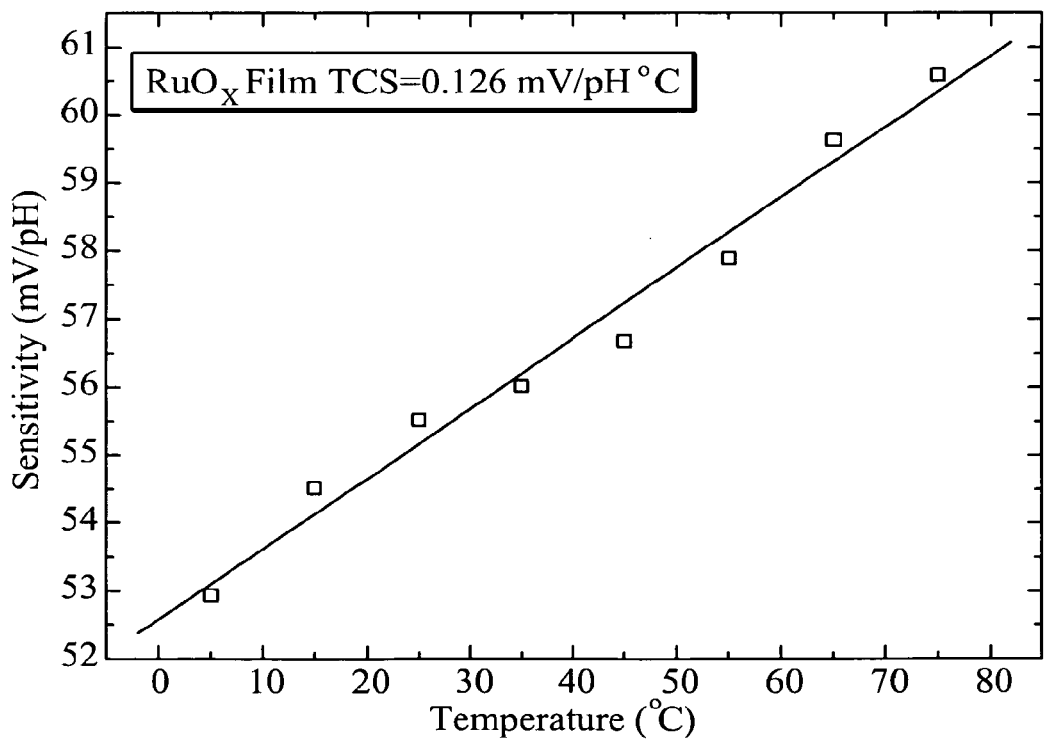
FIG. 35 shows a sensitivity curve of an embodiment of a ruthenium oxide film at various temperatures.
Figure 36:
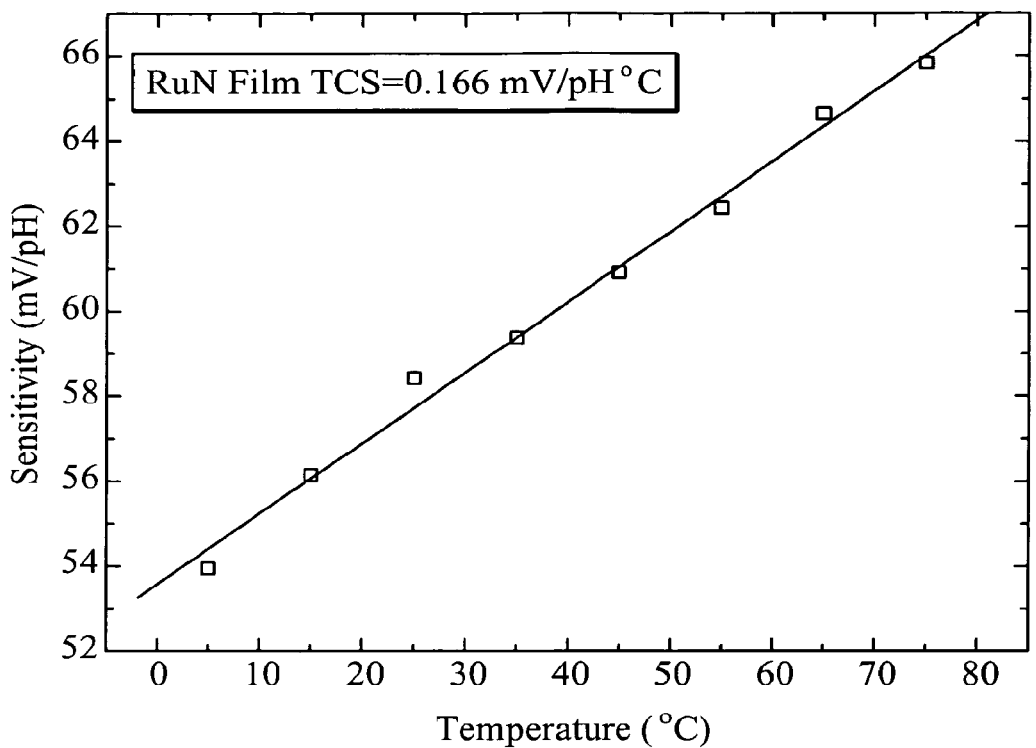
FIG. 36 shows a sensitivity curve of an embodiment of a ruthenium nitride film at various temperatures.

The results of Tables 3 and 4 can be drawn into FIGS. 35 and 36 respectively. The temperature coefficient of sensitivity (TCS) of the ruthenium oxide film is 0.126 mV/pH° C., and that of the ruthenium nitride 0.166 mV/pH° C. The actual values are slightly different from the linear regression, indicating temperature effect may interference the sensitivity. The extended gate structure may also be a factor of the temperature effect. The temperature effect may be remedied by ruthenium dioxide sputtering.

B. Drift Effect

The ruthenium-containing film was immersed in a standard solution at a constant temperature controlled by a temperature controller and the entire measuring system was placed in a dark box. The measuring system is shown in FIG. 3. The operating conditions were drain/source voltage ($V_{DS}$)=0.2 V and drain current ($I_D$)=5 μA. The results were recorded every minute by Voltage-Time recorder Data-chart 3000.

Drift values of the ruthenium-containing film were measured as follows. First, the biosensor was placed in a buffer solution at pH 1 for 12 hours, and the output voltage ($V_G$) was measured in accordance with the measuring system as shown in FIG. 4. The measuring steps were repeated with the biosensor placed in buffer solutions at various pH values. For the ruthenium oxide film, the pH values of the buffer solutions ranged from pH 1 to pH 12, while for the ruthenium nitride film, the pH values ranged from pH 1 to pH 13. The results are shown in Table 5.

TABLE 5

Drift values of the ruthenium-containing film

| pH | Drift value of $RuO_X$ film (mV/hour) | Drift value of RuN film (mV/hour) |
|---|---|---|
| 1 | 0.32 | 0.21 |
| 2 | 0.95 | 0.66 |
| 3 | 1.58 | 1.12 |
| 4 | 2.21 | 1.59 |
| 5 | 2.85 | 2.08 |
| 6 | 3.52 | 2.61 |
| 7 | 4.23 | 3.26 |
| 8 | 4.99 | 3.84 |
| 9 | 5.83 | 4.47 |
| 10 | 6.71 | 5.18 |
| 11 | 7.64 | 5.92 |
| 12 | 8.63 | 6.73 |
| 13 | — | 7.61 |

Figure 37:
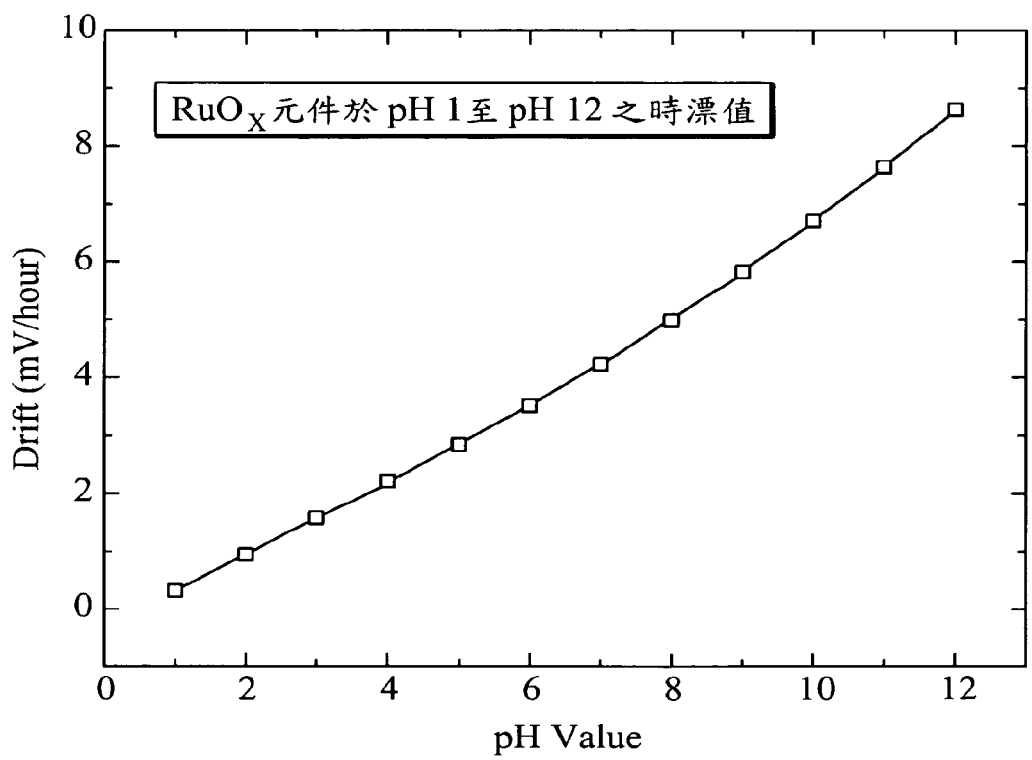
FIG. 37 shows the relationship between drift values and pH in an embodiment of a ruthenium oxide device at 25° C.
Figure 38:
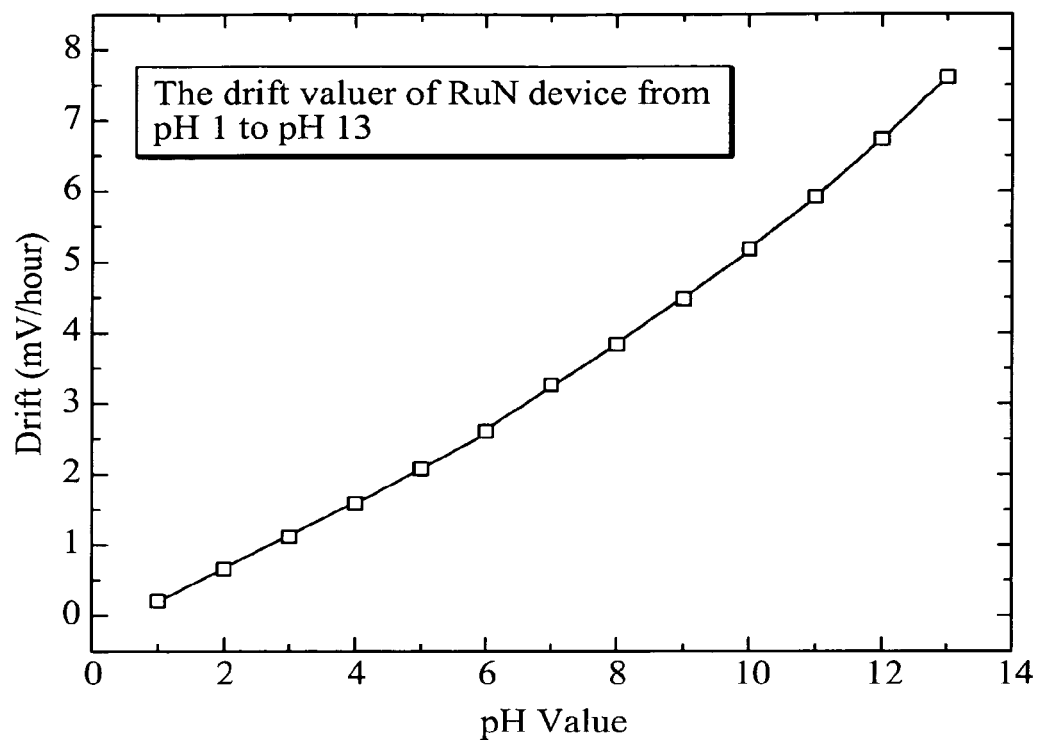
FIG. 38 shows the relationship between drift values and pH in an embodiment of a ruthenium nitride device at 25° C.

The results of Table 5 can be drawn to FIGS. 37 and 38 respectively. It was found that the drift effect of the ruthenium oxide and ruthenium nitride films was apparent in alkali solutions. Drift value increased with pH value. Hydrated-layer was formed mainly by OH⁻ ion. Concentration of OH⁻ ion and drift value decreased with pH value. This phenomenon can be found in all of the gate materials in use.

The drift value of the ruthenium oxide film is larger than that of the ruthenium nitride film. This may be due to the resistivity of the ruthenium oxide film exceeding that of the ruthenium nitride film. As shown in Table 2, the differences can be ten fold. In addition, the ruthenium oxide film has pseudo-capacitance and higher surface capacitance than the ruthenium nitride film. This RC delay effect makes the drift effect more apparent.

C. Hysteresis Effect

Figure 39:
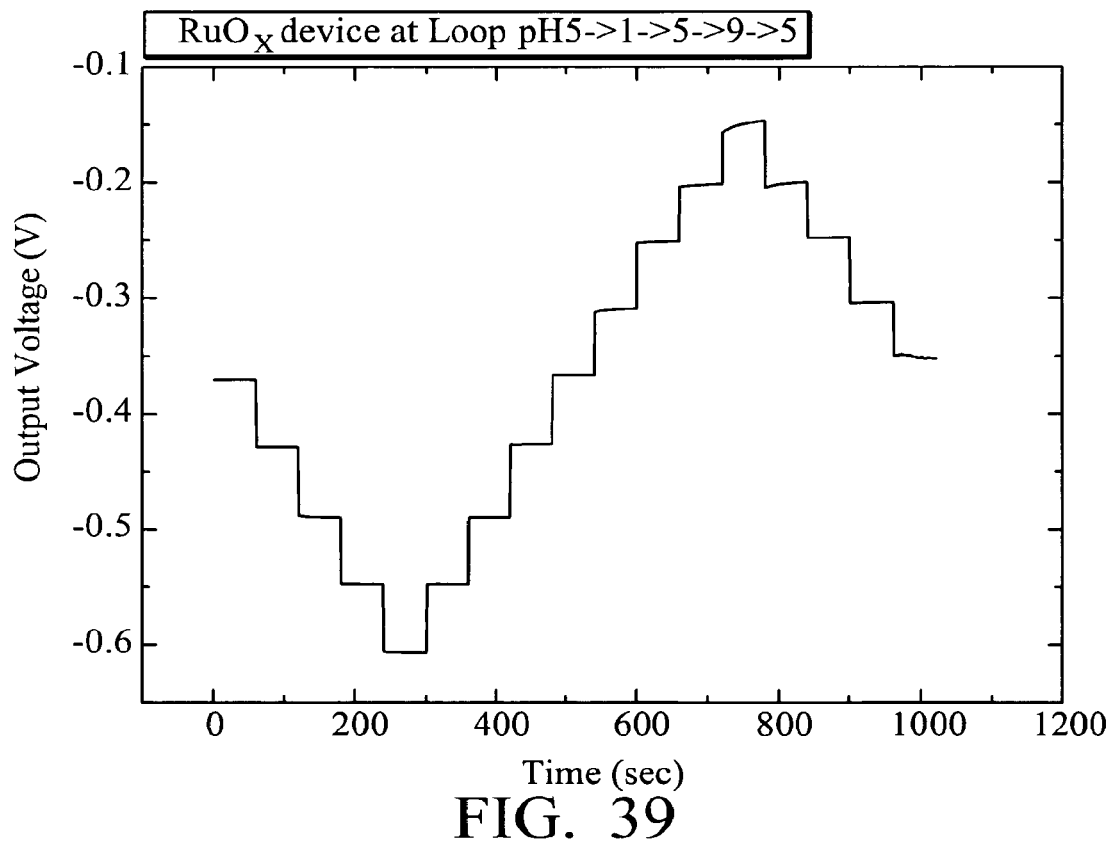
FIG. 39 shows the relationship between pH and time in hysteresis measurement of an embodiment of a ruthenium oxide device.
Figure 40:
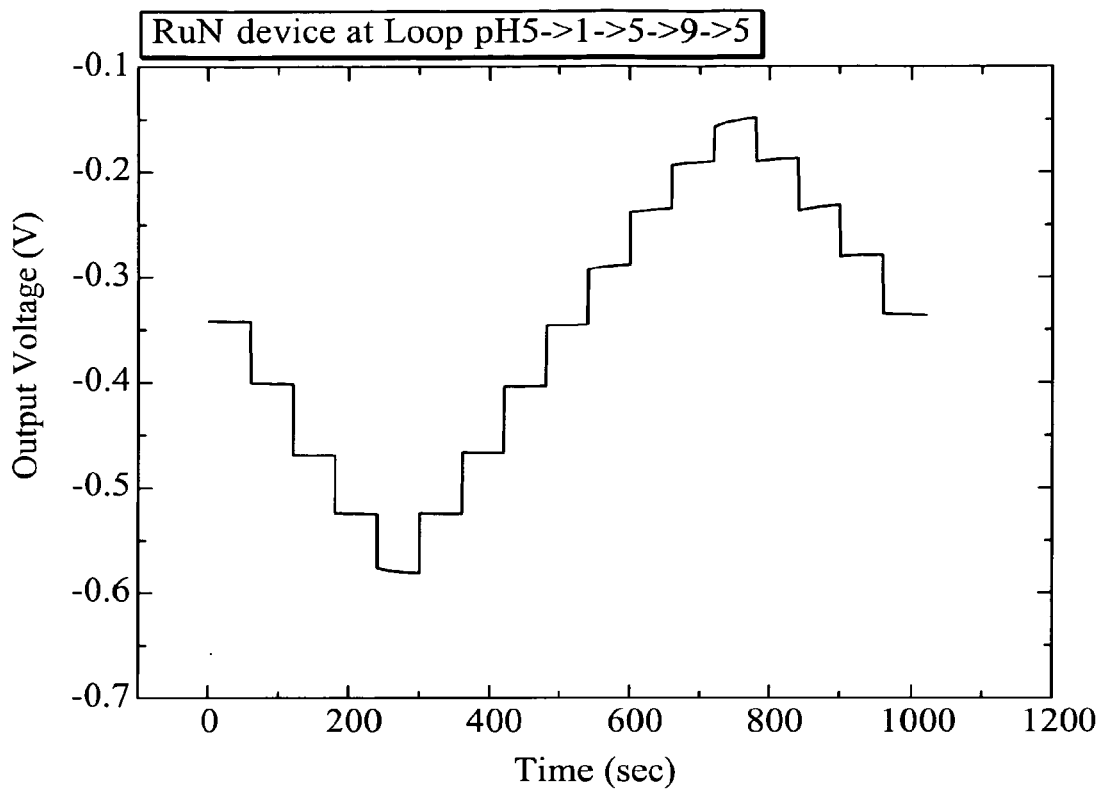
FIG. 40 shows the relationship of pH and time in hysteresis measurement of an embodiment of a ruthenium nitride device.

Hysteresis effect was measured with the same measuring system as drift effect, as shown in FIG. 4. The operating conditions were also the same. The hysteresis loop was set as pH 5→1→5→9→5. Measurements were carried out in the order of the hysteresis loop, and each measurement was set to one pH value per minute. The loop has 17 points for measurement and the loop time was 1020 seconds (17 minutes). The hysteresis curves of the ruthenium oxide and ruthenium nitride films are shown in FIGS. 39 and 40 respectively. The results of the measurement time of 2 or 4 minutes were also recorded. The loop time for 2 or 4 minutes was 2040 or 4080 seconds respectively.

Figure 41:
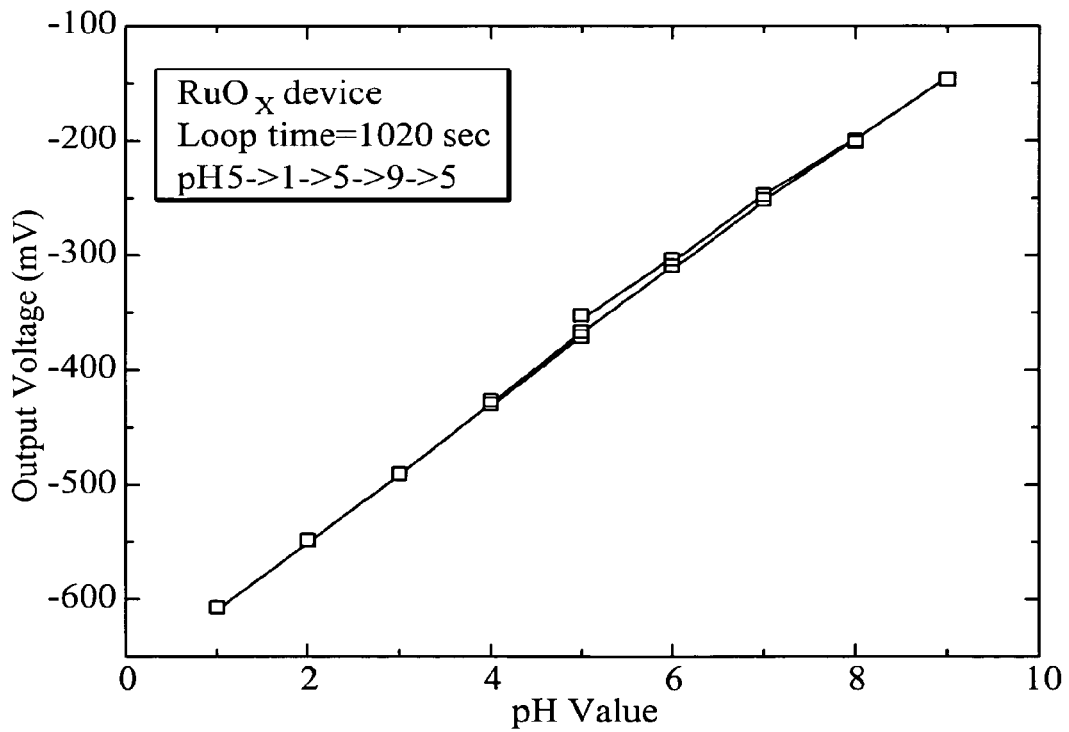
FIG. 41 shows a hysteresis curve of an embodiment of a ruthenium oxide device. Hysteresis value=18.31 mV.
Figure 42:
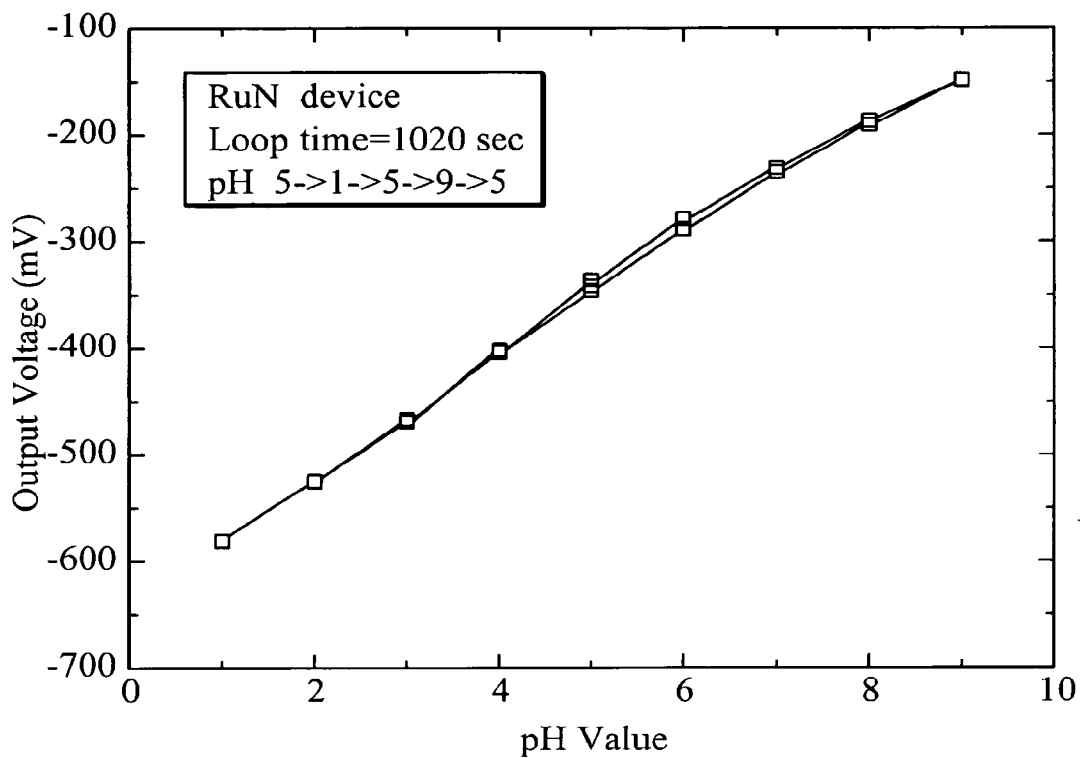
FIG. 42 shows a hysteresis curve of an embodiment of a ruthenium nitride device. Hysteresis value=5.43 mV.
Figure 43:
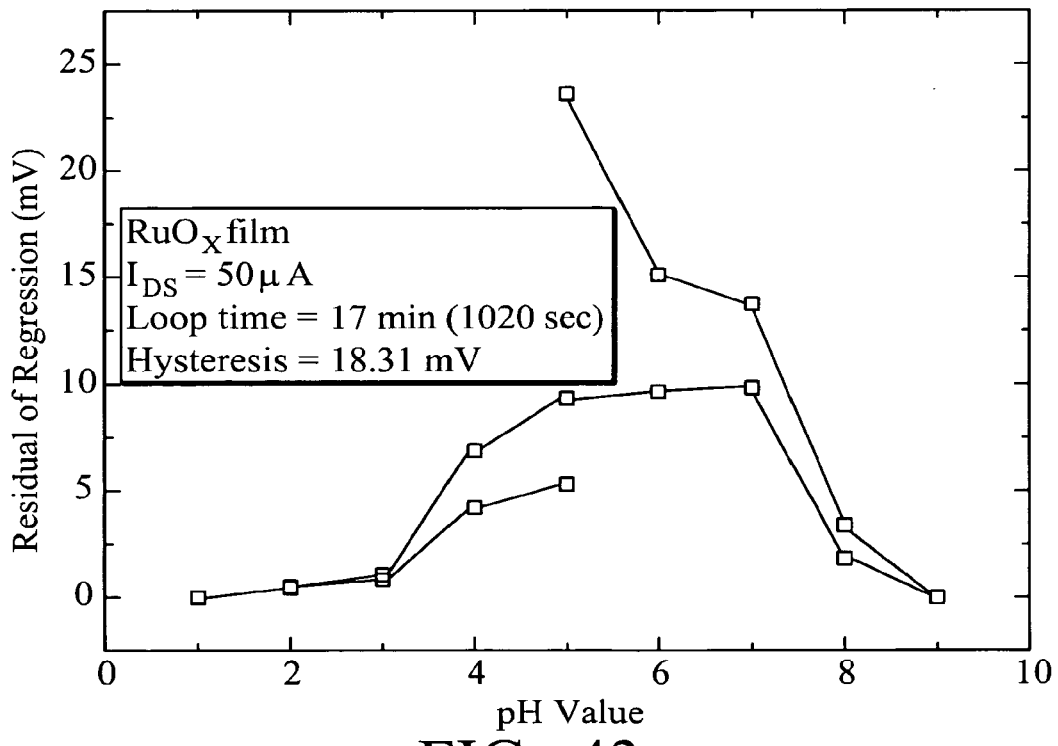
FIG. 43 shows a residual regression diagram of an embodiment of a ruthenium oxide device at loop time of 1020 seconds.
Figure 44:
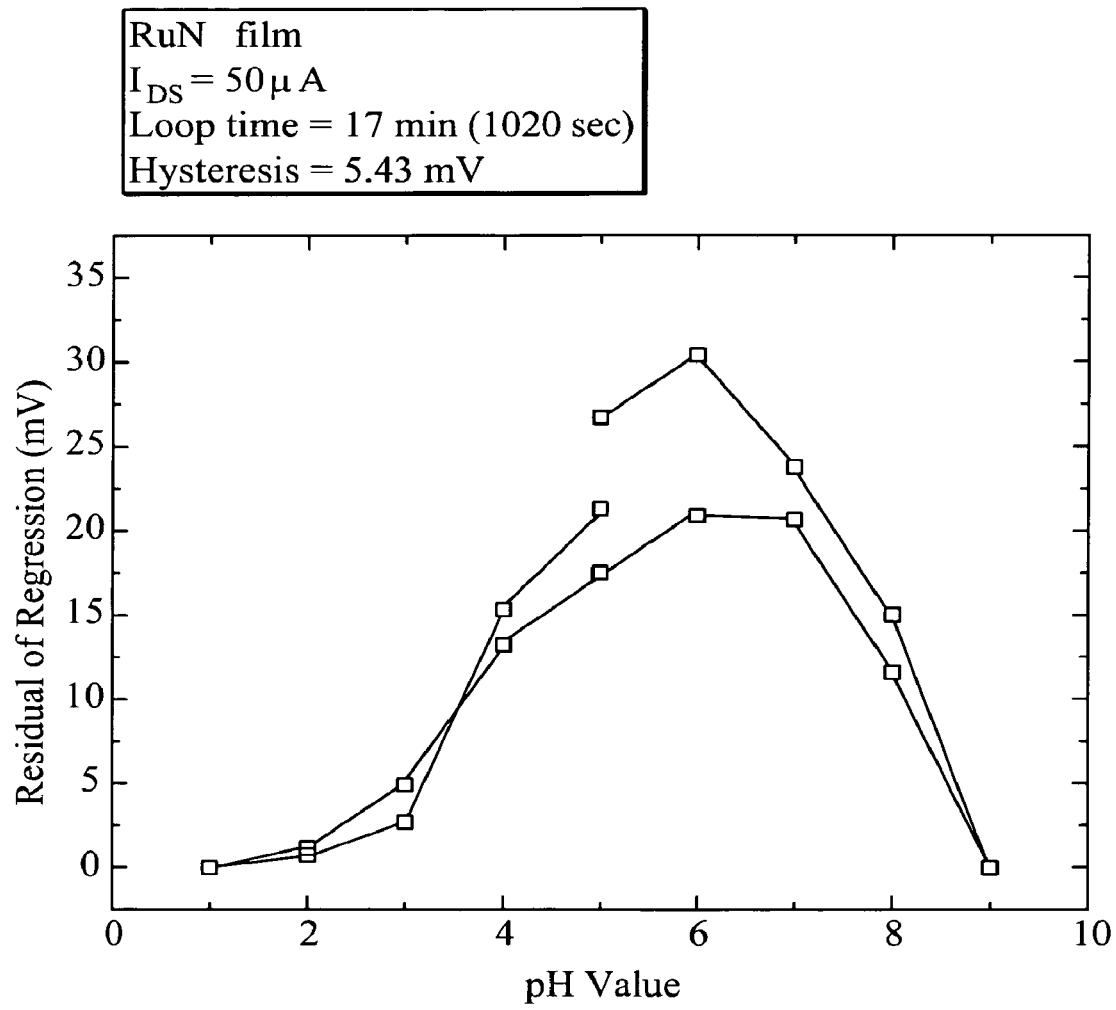
FIG. 44 shows a residual regression diagram of an embodiment of a ruthenium nitride device at loop time of 1020 seconds.

The results of the ruthenium oxide and ruthenium nitride films are shown in FIGS. 41 and 42 respectively. FIGS. 41 and 42 are converted to residual of regression of hysteresis value as shown in FIGS. 43 and 44 respectively to obtain the hysteresis width of the two ruthenium-containing films. The residual regression of hysteresis value was obtained as follows. First, the line was plotted between pH 1 and pH 9 to form the basis line. The relative differences were calculated between the actual voltages and the basis line, and the relationship of the relative differences and pH values were the residual regression.

As shown in FIGS. 43 and 44, it was clear that the hysteresis value of the ruthenium oxide film was 18.31 mV and that of the ruthenium nitride film was 5.43 mV. The ruthenium oxide film has pseudo-capacitance, leading to an apparent hysteresis effect. The biosensor is suggested to be a disposable product.

D. Lifespan Analysis

The factors affecting the lifespan of the biosensor include operational stability and storage stability.

The operational stability was measured by continuous operation of the biosensor and the results are shown in Table 6.

TABLE 6

Continuous operation of the biosensor

| Continuous operation (hour) | $RuO_X$ film | RuN film |
|---|---|---|
| 0 | 56.42 | 58.09 |
| 12 | 55.63 | 57.73 |
| 24 | 54.26 | 57.42 |
| 36 | Poor sensitivity | 56.84 |
| 48 | Poor sensitivity | 55.88 |

Figure 45:
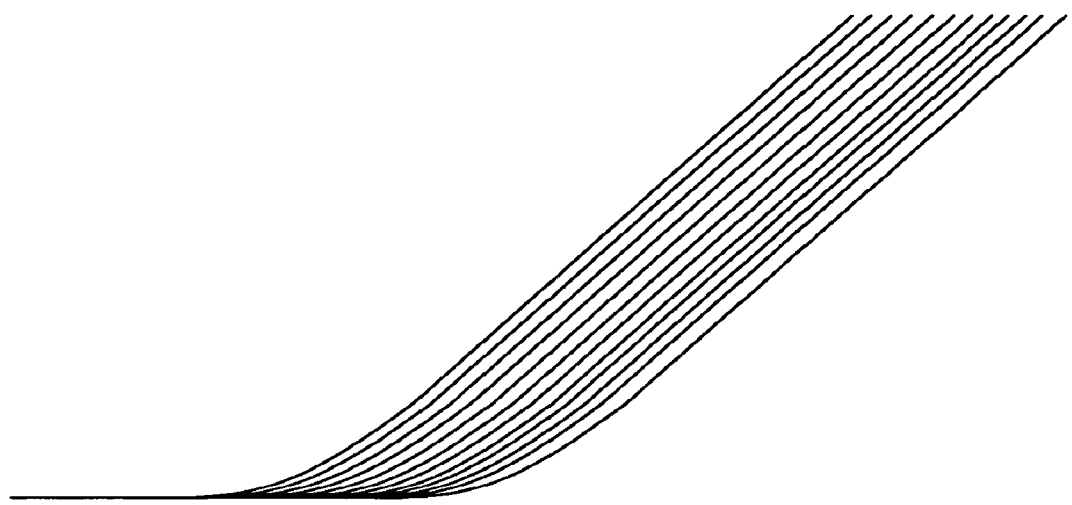
FIG. 45 shows I-V curves of an embodiment of a ruthenium oxide device in an enlarged scale at the initial operation.
Figure 46:
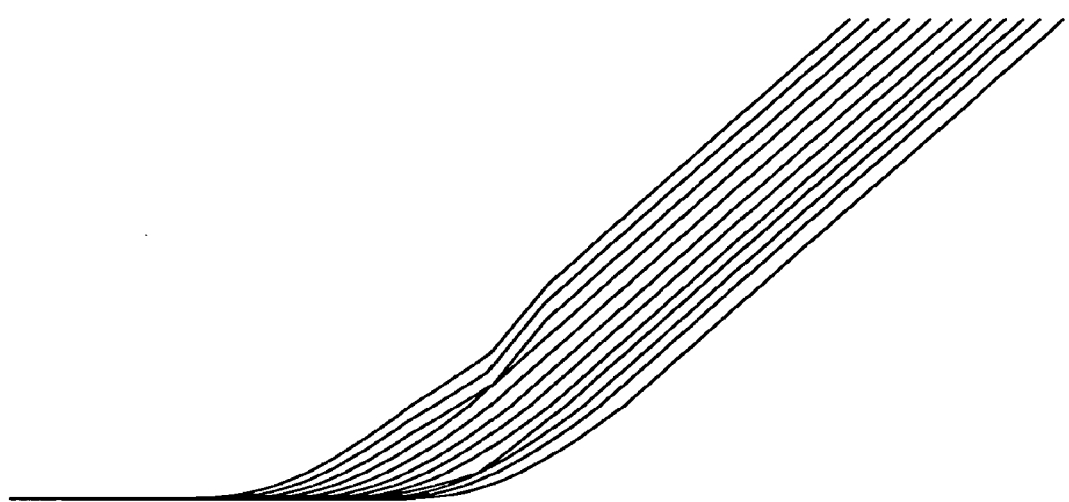
FIG. 46 shows I-V curves of an embodiment of a ruthenium oxide device in an enlarged scale after 12-hour continuous operation.
Figure 47:
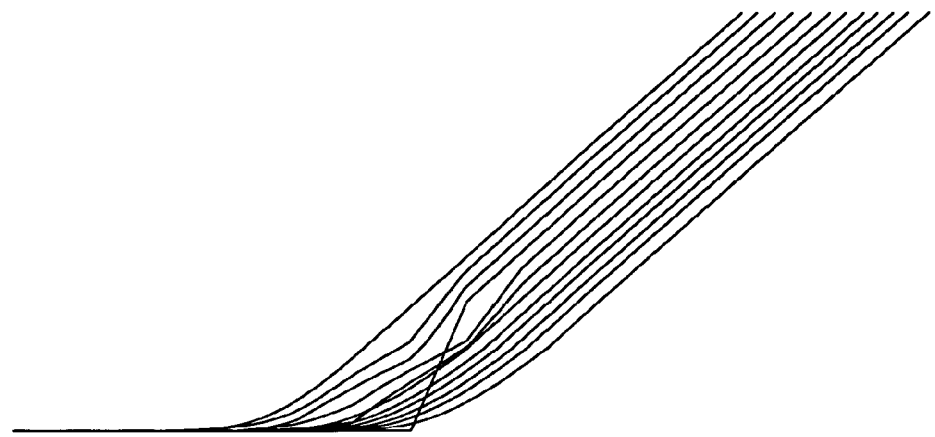
FIG. 47 shows I-V curves of an embodiment of a ruthenium oxide device in an enlarged scale after 24-hour continuous operation.
Figure 48:
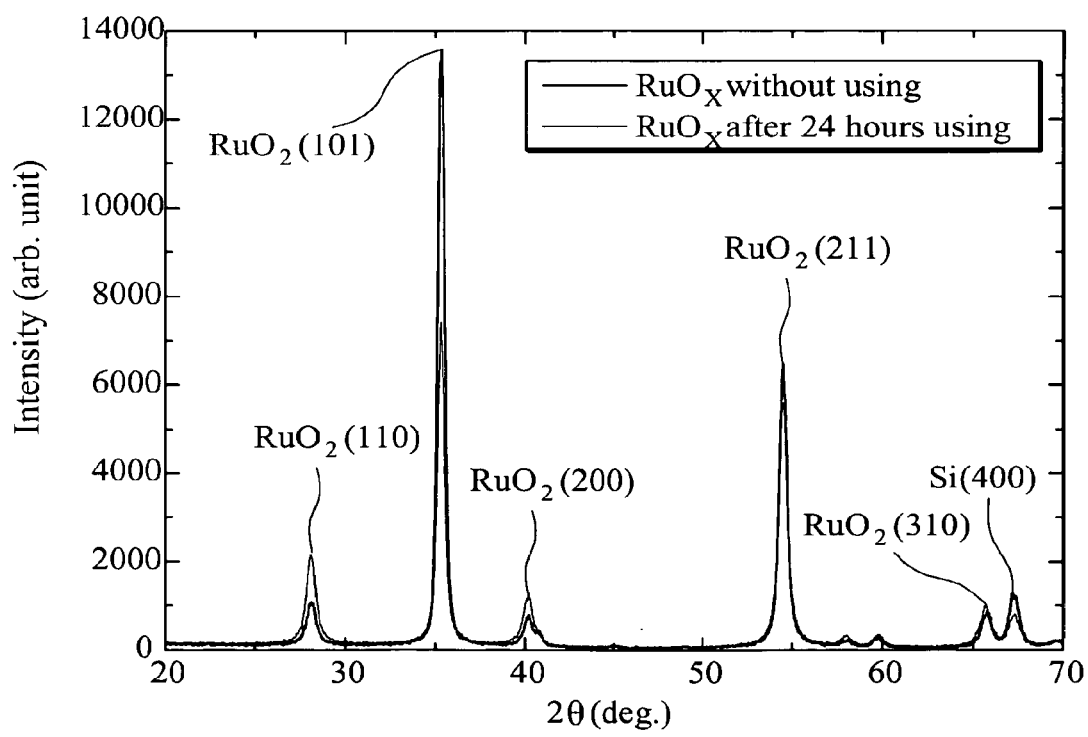
FIG. 48 shows XRD comparison pattern of an embodiment of a ruthenium oxide film (thickness=1670 nm) in the curves of direct operation and 24-hour operation conditions.
Figure 49:
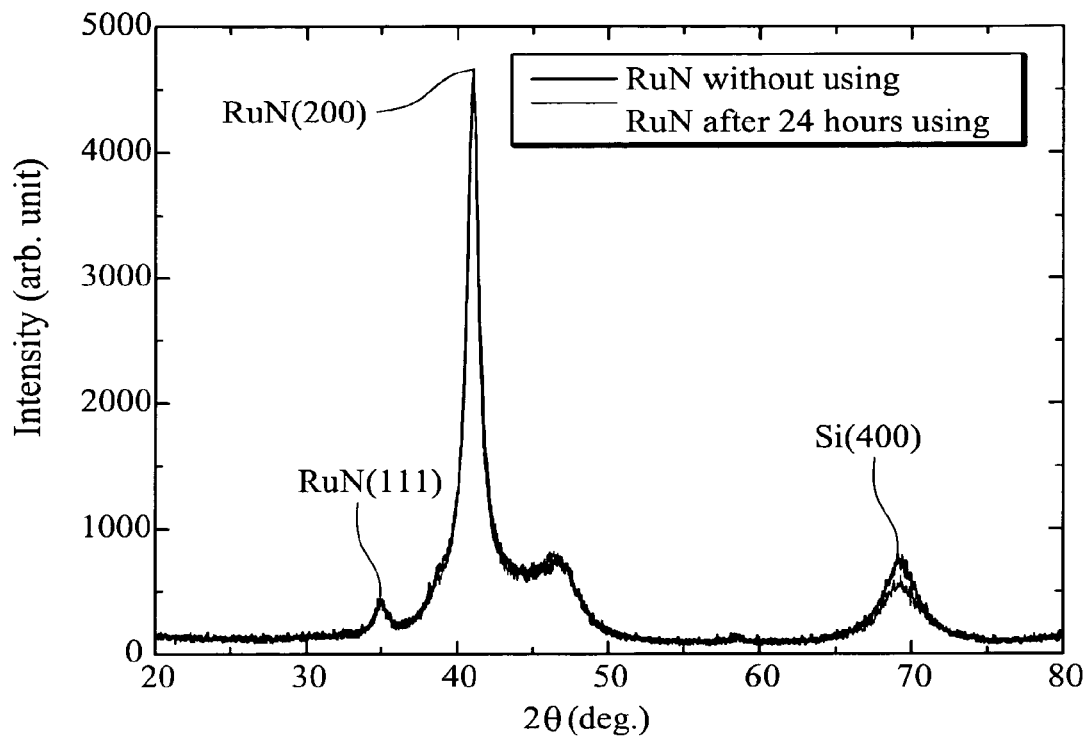
FIG. 49 shows XRD comparison pattern of an embodiment of a ruthenium nitride film (thickness=574.2 nm) in the curves of direct operation and 24-hour operation conditions.

With the results of the ruthenium oxide film in FIGS. 45, 46, and 47, it was found that the linearity becomes rough and poorly linear with the continuous operation. At about 30 hours, the curve was destroyed at pH 4 and pH 10. On the contrary, the biosensor containing the ruthenium nitride film could be operated for 48 hours. The crystallographic direction of the biosensor at the initial or after 24-hour operation was measured by X-Ray Diffraction (XRD), and the results are shown in FIG. 48. It was found that the grain orientation of $RuO_2(101)$ decayed quickly during the redox reaction. On the contrary, the grain orientation of RuN was almost intact, and the biosensor containing the ruthenium nitride has a longer lifespan.

Figure 50:
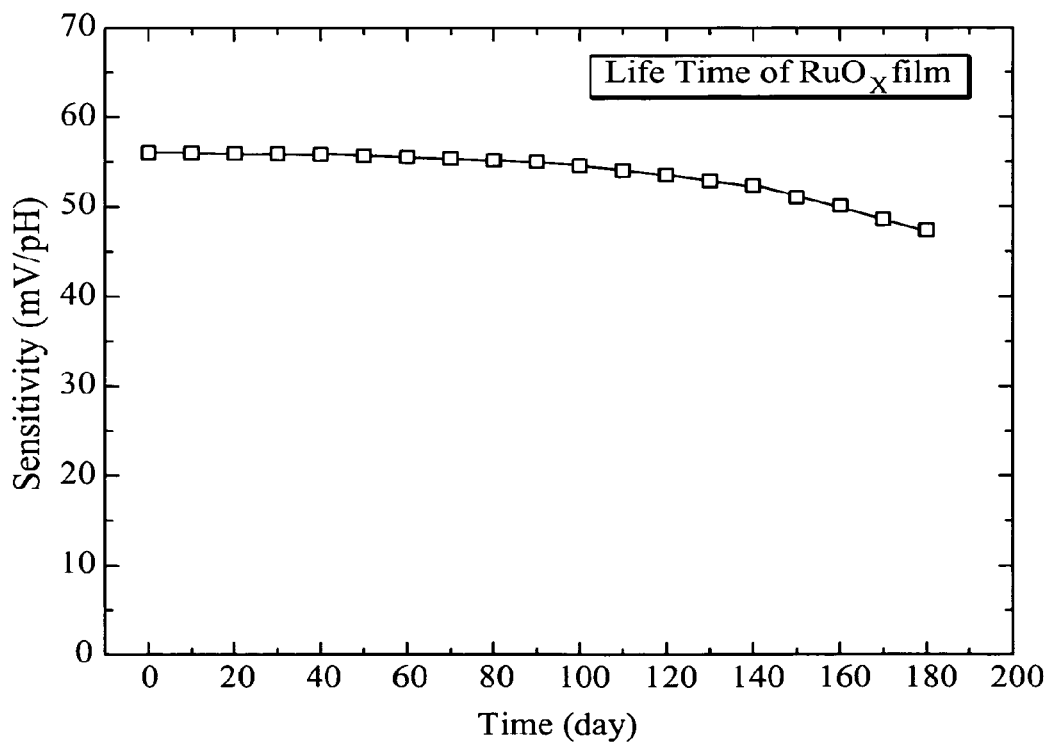
FIG. 50 shows the sensitivity changes in an embodiment of a ruthenium oxide film at various storage time points.

Storage stability was tested as follows. The biosensor was stored in a moisture-proof case. The sensitivity of the biosensor was measured every ten days and the results are shown in FIG. 50. The results of every month are listed in Table 7. The sensitivity of the biosensor containing the ruthenium nitride film may overlap at pH 10 and pH 11 after 6-month storage. The sensitivity of the ruthenium-containing biosensor changes with storage time, indicating the sensing film may have oxidation with air. It is suggested the biosensor be stored in vacuum packing.

TABLE 7

Storage stability of the biosensor

| Storage stability | $RuO_X$ film | RuN film |
|---|---|---|
| After sputtering | 56.02 | 58.42 |
| After one month | 55.89 | 58.31 |
| After two months | 55.53 | 58.25 |
| After three months | 55.01 | 57.05 |
| After four months | 53.52 | 55.67 |
| | | (pH 10 and pH 11 close to each other) |
| After five months | 51.02 | 53.31 |
| | | (pH 10 and pH 11 close to each other) |
| After six months | 47.41 | pH 10 and pH 11 overlapped |

Example 5

Vitamin C Biosensor Prepared with the Ruthenium-Containing Biosensor 3-glycidoxypropyltrimethoxysilane (GPTS) was used to immobilize ascorbate oxidase on the biosensor containing the ruthenium oxide film. The chemicals are as follows.

a. Ascorbate oxidase, EC1.10.3.3, powder, purchased by Sigma Chemical Company, stored at 2° C.-8° C.

b. L-Ascorbic acid (Vitamin C), A 0332, powder, purchased by Sigma Chemical Company, $C_6H_8O_6$, M.W.=176.

c. $KH_2PO_4$ (potassium phosphate)=136.09, purchased by Sigma Chemical Company, for the preparation of Phosphate Buffer Solution (PBS).

The ascorbate oxidase was immobilized on the surface of the ruthenium oxide film by 3-glycidoxypropyltrimethoxysilane (GPTS). First, the biosensor was washed with a neutral detergent or methyl alcohol under 10-minute ultrasound shaking to remove contaminants from the surface of the sensing film. The biosensor was then washed with deionized water. Two μL of 10% GPTS solution containing GPTS:toluene of 10:90 in volume were dipped on the surface of the sensing film. The biosensor was baked at ° C. for 2 hours and immersed in PBS at pH 7.6 for 15 minutes to remove the unimmobilized GPTS. The ascorbate oxidase solution was prepared by dissolving 14 mg of ascorbate oxidase in 100 μL of 5 mM PBS at pH 7.6. The ascorbate oxidase solution was dipped on the surface of the sensing film and incubated for 12 hours. The biosensor was then immersed in 5 mM PBS at pH 7.6 for 5 minutes three times to remove unlinked ascorbate oxidase. The vitamin C biosensor was obtained.

Vitamin C test solutions in PBS with a concentration of 5 mM, 10 mM, 15 mM, 20 mM, 25 mM, 30 mM, 35 mM, 40 mM, 45 mM, and 50 mM were prepared by serial dilution and stored at 4° C. before testing.

Figure 51:
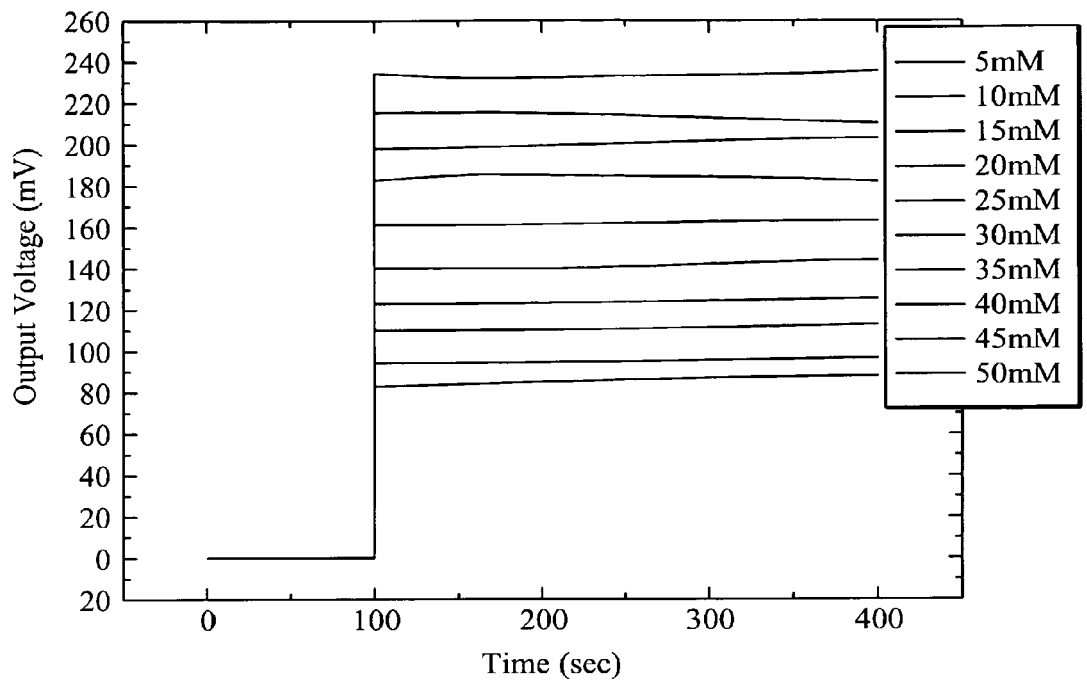
FIG. 51 shows the measurement of an embodiment of a ruthenium-containing device combined with ascorbate oxidase for the detection of 5, 10, 15, 20, 25, 30, 35, 40, 45, and 50 mM of ascorbic acid.
Figure 52:
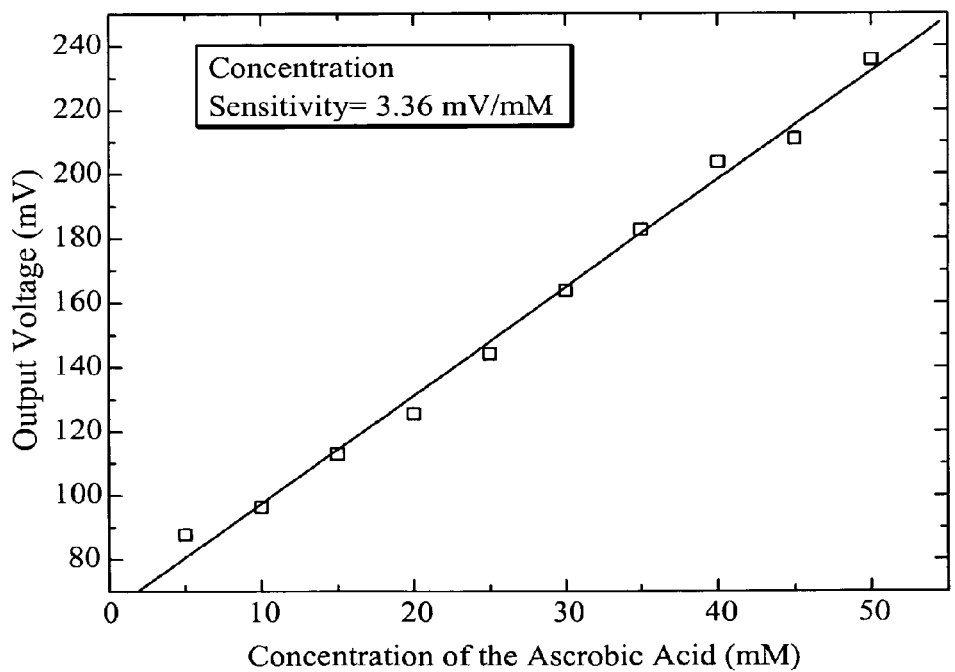
FIG. 52 shows the concentration sensitivity of an embodiment of a ruthenium-containing device combined with ascorbate oxidase.
Figure 53:
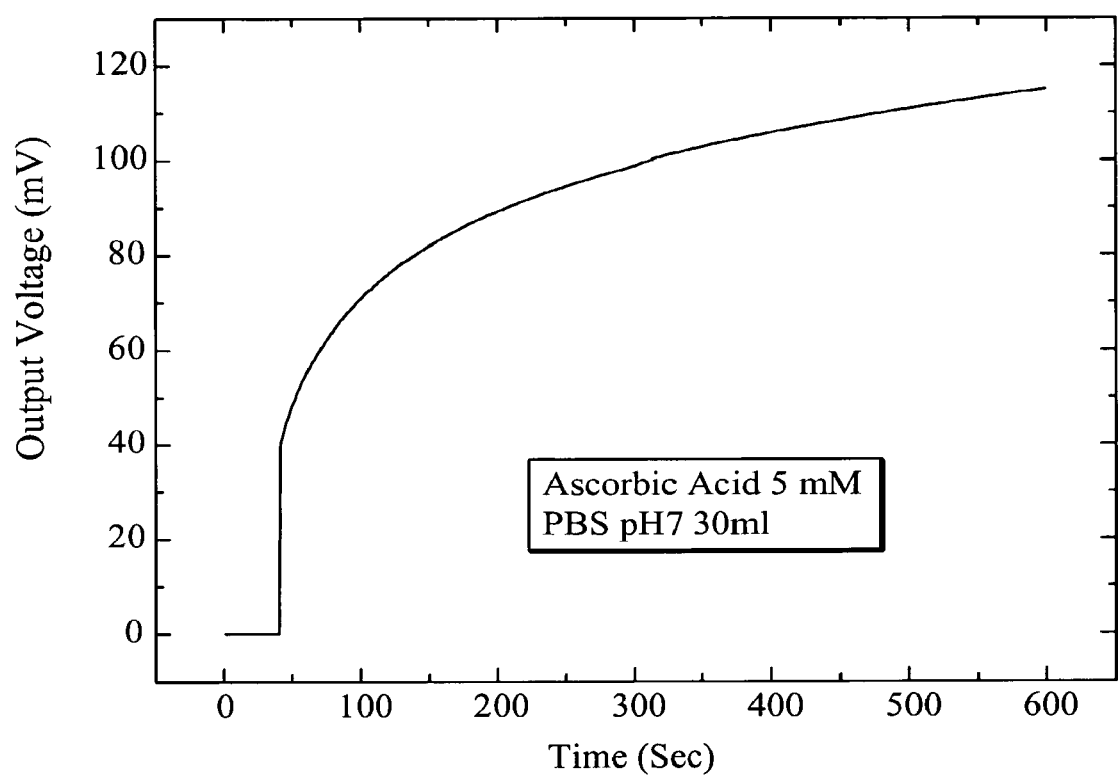
FIG. 53 shows measurement results of an embodiment of a ruthenium-containing device combined with ascorbate oxidase in 5 mM ascorbic acid in PBS.

The prepared vitamin C biosensor was tested in the vitamin C test solutions and the results are shown in FIG. 51. The sensitivity of the vitamin C biosensor is 3.36 mV/mM, as shown in FIG. 52. The vitamin C biosensor with PVA-SbQ-immobilized ascorbate oxidase was also tested in 5 mM vitamin C test solution and the results are shown in FIG. 53. The vitamin C biosensor immobilized by GPTS has faster response time than that immobilized by pVA-SbQ since GPST is thinner than PVA-SbQ. The biosensor immobilized by GPTS has the advantages of quick response time and long lifespan.

The device models for the vitamin C biosensor were proposed as shown in FIGS. 54 and 55 in which the pH and vitamin C biosensors can be integrated to form one biosensor. The optimal pH value for the operation of the vitamin C biosensor is pH 6-7. With the consideration of the optimal pH value of the immobilization using GPTS (over pH 7), the optimal pH value for the vitamin C biosensor was set as pH 7.6. The combination of the function of pH and vitamin C biosensors may contribute the requirement of pH value adjustment.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A vitamin C biosensor with an extended gate field effect transistor structure, comprising:
   a metal oxide semiconductor field effect transistor (MOSFET);
   a first extended gate to act as a first sensing unit, comprising a first substrate, and a first ruthenium-containing film thereon;
   a second extended gate to act as a second sensing unit comprising a second substrate, a second ruthenium-containing film thereon, and a ascorbate oxidase film immobilized on the second ruthenium-containing film; and
   a conductive wire connecting the MOSFET and the first and the second sensing units.

2. The vitamin C biosensor as claimed in claim 1, wherein the first and the second MOSFET are n-type.

3. The vitamin C biosensor as claimed in claim 1, wherein the conductive wire connects the gate of the MOSFET and the first and second sensing units.

4. The vitamin C biosensor as claimed in claim 1, wherein the first and second substrates are silicon.

5. The vitamin C biosensor as claimed in claim 1, wherein the first and second ruthenium-containing films are ruthenium oxide (RuOX).

6. The vitamin C biosensor as claimed in claim 1, wherein the first and second ruthenium-containing films are ruthenium nitride (RuN).

7. The vitamin C biosensor as claimed in claim 1, wherein the ascorbate oxidase is immobilized by 3-glycidoxypropyltrimethoxysilane (GPTS).

8. The vitamin C biosensor as claimed in claim 7, wherein GPTS is premixed with toluene in a ratio of GPTS:toluene=10:90.

9. The vitamin C biosensor as claimed in claim 1, further comprising an insulating layer covering the surface of the first and second sensing units and exposing the first ruthenium-containing film and the ascorbate oxidase film respectively.

10. The vitamin C biosensor as claimed in claim 1, wherein the first biosensor detects pH value and the second biosensor detects the vitamin C concentration.

* * * * *